(12) United States Patent
Nguyen et al.

(10) Patent No.: US 12,697,068 B2
(45) Date of Patent: Aug. 4, 2026

(54) SYSTEMS AND METHODS FOR TOURNIQUET OPERATION AND CONTROL

(71) Applicant: The General Hospital Corporation, Boston, MA (US)

(72) Inventors: John Quan Nguyen, Pomona, CA (US); Avery Lee Goss, Pelham, NH (US); Conor Lee Evans, Charlestown, PA (US); Lilian Witthauer, Flueh (CH); Matthias Muller, Bonndorf (DE)

(73) Assignee: The General Hospital Corporation, Boston, MA (US)

( * ) Notice: Subject to any disclaimer, the term of this patent is extended or adjusted under 35 U.S.C. 154(b) by 720 days.

(21) Appl. No.: 17/633,521

(22) PCT Filed: Aug. 7, 2020

(86) PCT No.: PCT/US2020/045500
§ 371 (c)(1),
(2) Date: Feb. 7, 2022

(87) PCT Pub. No.: WO2021/041006
PCT Pub. Date: Mar. 4, 2021

(65) Prior Publication Data
US 2022/0346717 A1     Nov. 3, 2022

Related U.S. Application Data

(60) Provisional application No. 62/884,010, filed on Aug. 7, 2019.

(51) Int. Cl.
| *A61B 5/00* | (2006.01) |
| *A61B 5/01* | (2006.01) |
| *A61B 5/1455* | (2006.01) |

(52) U.S. Cl.
CPC .............. *A61B 5/6843* (2013.01); *A61B 5/01* (2013.01); *A61B 5/14551* (2013.01);
(Continued)

(58) Field of Classification Search
CPC .............. A61B 17/132; A61B 17/1322; A61B 17/1327; A61B 17/135; A61B 17/1355;
(Continued)

(56) References Cited

U.S. PATENT DOCUMENTS

| 4,106,002 A | 8/1978 | Hogue, Jr. |
| 7,938,846 B2 | 5/2011 | Akerfeldt et al. |
(Continued)

FOREIGN PATENT DOCUMENTS

| EP | 4009882 A2 | 6/2022 | |
| WO | WO-2011053787 A2 * | 5/2011 | ......... A61B 10/0045 |
(Continued)

OTHER PUBLICATIONS

International Search Report, "International Search Report and Written Opinion of the International Searching Authority," International Application No. PCT/US2020/045500, mailed Feb. 24, 2021, 12 pages.
(Continued)

*Primary Examiner* — Kankindi Rwego
(74) *Attorney, Agent, or Firm* — QUARLES & BRADY LLP

(57) ABSTRACT

Systems and methods for tourniquet monitoring and control is provided. A system includes at least one sensor, a housing, a processor, and a user communication module. The at least one sensor is configured to monitor at least one of deployment or operation of the tourniquet. The housing is configured to removably engage the tourniquet to position the at least one sensor to monitor the at least one of deployment or operation of the tourniquet. The processor is configured to
(Continued)

receive feedback from the at least one sensor, compare the feedback to at least one of deployment or operation parameters for the tourniquet, and generate a user report. The user communication module is configured to communicate the user report.

32 Claims, 12 Drawing Sheets

(52) U.S. Cl.
CPC ............ *A61B 5/6831* (2013.01); *A61B 5/685* (2013.01); *A61B 5/746* (2013.01); *A61B 2505/01* (2013.01)

(58) Field of Classification Search
CPC ... A61B 5/02438; A61B 5/026; A61B 5/6831; A61B 5/02; A61B 5/02042; A61B 5/02233; A61B 5/0261; A61B 5/11; A61B 5/1114; A61B 5/01; A61B 5/14551; A61B 5/683; A61B 5/6843; A61B 5/685; A61B 5/746; A61B 2505/01
USPC ....................................................... 606/203
See application file for complete search history.

(56) References Cited

U.S. PATENT DOCUMENTS

| | | | |
|---|---|---|---|
| 8,764,685 | B2 | 7/2014 | Casey |
| 2004/0147956 | A1 | 7/2004 | Hovanes et al. |

| | | | | |
|---|---|---|---|---|
| 2007/0049853 | A1* | 3/2007 | Adams ................. | A61H 9/0078 |
| | | | | 601/149 |
| 2008/0177159 | A1 | 7/2008 | Gavriely | |
| 2008/0319328 | A1* | 12/2008 | Akerfeldt ............. | A61B 17/135 |
| | | | | 600/494 |
| 2009/0312615 | A1* | 12/2009 | Caduff ................. | A61B 5/0531 |
| | | | | 600/347 |
| 2010/0234877 | A1 | 9/2010 | Pienkowski et al. | |
| 2010/0241032 | A1 | 9/2010 | Lee et al. | |
| 2011/0251636 | A1* | 10/2011 | McEwen ................. | A61B 8/06 |
| | | | | 606/202 |
| 2012/0330192 | A1 | 12/2012 | Casey | |
| 2015/0309563 | A1* | 10/2015 | Connor ................ | A61B 5/1071 |
| | | | | 73/865.4 |
| 2015/0335288 | A1* | 11/2015 | Toth ..................... | A61B 5/6833 |
| | | | | 600/391 |
| 2017/0273694 | A1 | 9/2017 | Lynch et al. | |
| 2017/0312161 | A1 | 11/2017 | Johnson et al. | |
| 2018/0153557 | A1 | 6/2018 | Dimino et al. | |
| 2018/0193031 | A1 | 7/2018 | Du et al. | |
| 2018/0271411 | A1* | 9/2018 | Ashkenazi ......... | A61B 5/14556 |

FOREIGN PATENT DOCUMENTS

| | | |
|---|---|---|
| WO | 2018108924 A1 | 6/2018 |
| WO | 2021041006 A2 | 3/2021 |

OTHER PUBLICATIONS

European Patent Office, Extended Search Report, Application No. 20858711.3, Jul. 5, 2023, 10 pages.

\* cited by examiner

220

265

266

220

265

266

272

SYSTEMS AND METHODS FOR TOURNIQUET OPERATION AND CONTROL

CROSS REFERENCE TO RELATED APPLICATIONS

This application is a U.S. National Stage of PCT Application No. PCT/US2020/045500 filed on Aug. 7, 2020 which is based on, claims priority to, and incorporates herein by reference in its entirety, U.S. Provisional Patent Application Ser. No. 62/884,010, filed on Aug. 7, 2019.

STATEMENT REGARDING FEDERALLY FUNDED RESEARCH

This invention was made with government support under HU0001-17-2-0009 awarded by the Uniform Services University of Health Sciences through the Henry Jackson Foundation. The government may have certain rights in the invention.

BACKGROUND

Emergency tourniquets are designed to apply circumferential pressure proximate to traumatic limb injuries to stop severe arterial bleeding prior to definitive care. Their use by properly trained and equipped ambulatory healthcare and military personnel has helped to dramatically reduce field, including battlefield, deaths. Though long used in battlefield settings, emergency tourniquets have recently gained popularity in the civilian sector, with just-in-time, point-of-injury, pre-hospital use increasing by tenfold over the past decade. However, even trained individuals can find it difficult to assess proper tourniquet application. For example, unrecognized under-tightened tourniquets will fail to adequately control blood flow, potentially leading to death. To further complicate the issue, prolonged use of properly-tightened tourniquets can promote additional injuries. For example, after six to eight hours of use, the risk of severe injury such as acute extremity compartment syndrome or limb loss markedly increases. Unrecognized over-tightened tourniquets can reduce this time-to-injury window significantly, leading to further limb trauma and the loss of the limb.

Typically, a tourniquet is deemed sufficiently tightened through cursory assessment of indicators, such as a lack of pulse or visual confirmation that bleeding has stopped. These indicators, however, are not always accurate and are difficult to assess during chaotic-battlefield and mass-casualty events, where fast and effective tourniquet application by both trained and untrained personnel can contribute significantly to saving lives.

In light of the above, it would be desirable to provide systems and methods for improved tourniquet operation and control, such as assistance for improved tourniquet deployment, use, and extended operation.

SUMMARY

The systems and methods of the present disclosure overcome the above and other drawbacks by providing a portable self-contained force and/or tissue oxygenation sensing toolkit that can be integrated with pre-existing, standard-of-care emergency tourniquets. The easy-to-use device would allow for the real-time monitoring of applied tourniquet pressure and/or tissue oxygenation along with tracking the time elapsed since a successful application.

In accordance with one aspect of the disclosure, a tourniquet monitoring system is provided. The system includes at least one sensor, a housing, a processor, and a user communication module. The at least one sensor is configured to monitor at least one of deployment or operation of a tourniquet. The housing is configured to removably engage the tourniquet to position the at least one sensor to monitor the at least one of deployment or operation of the tourniquet. The processor is configured to receive feedback from the at least one sensor, compare the feedback to at least one of deployment or operation parameters for the tourniquet, and generate a user report. The user communication module is configured to communicate the user report.

In accordance with another aspect of the disclosure, a method for monitoring occlusive effect of a tourniquet on a human limb is provided. The method includes providing a tourniquet and retrofitting a system onto the tourniquet by removably attaching a housing of the system to the tourniquet. The system includes the housing, a pressure sensor supported by the housing, a processor, and a user communication module. The method also includes tightening the tourniquet around the human limb so that the pressure sensor is interposed between the tourniquet and the human limb, sensing a compressive force between the tourniquet and the human limb via the pressure sensor, and monitoring an elapsed time from when the tourniquet is tightened around the human limb. The method further includes communicating a user report via the user communication module, the user report including at least one of the compressive force and the elapsed time.

In accordance with yet another aspect of the disclosure, a tourniquet system for use on a human limb is provided. The system includes a field tourniquet, a housing configured to removably engage the tourniquet, a pressure sensor, an oxygenation sensor, a processor, and a user communication module. The pressure sensor is positioned relative to the housing and the tourniquet so the pressure sensor is interposed between the tourniquet and the human limb for sensing compressive force therebetween when the housing is engaged with the tourniquet. The oxygenation sensor is positioned relative to the housing and the tourniquet so the pressure sensor is interposed between the tourniquet and the human limb for sensing oxygen levels of the human limb when housing is engaged with the tourniquet. The processor is configured to receive feedback from the pressure sensor and the oxygenation sensor, compare the feedback to at least one of deployment or operation parameters for the tourniquet, and generate a user report. The user communication module is configured to communicate the user report.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 7A illustrates the sensor deployment system in an undeployed state; FIG. 7B illustrates one type of sensor deployment system in a deployed state; FIG. 7C illustrates another type of sensor deployment system in a deployed state; FIG. 7D illustrates yet another type of sensor deployment system in an undeployed state; FIG. 7E illustrates yet another type of sensor deployment system in an undeployed state; and FIG. 7F illustrate yet another type of sensor deployment system in an undeployed state.

DETAILED DESCRIPTION

Figure 1:
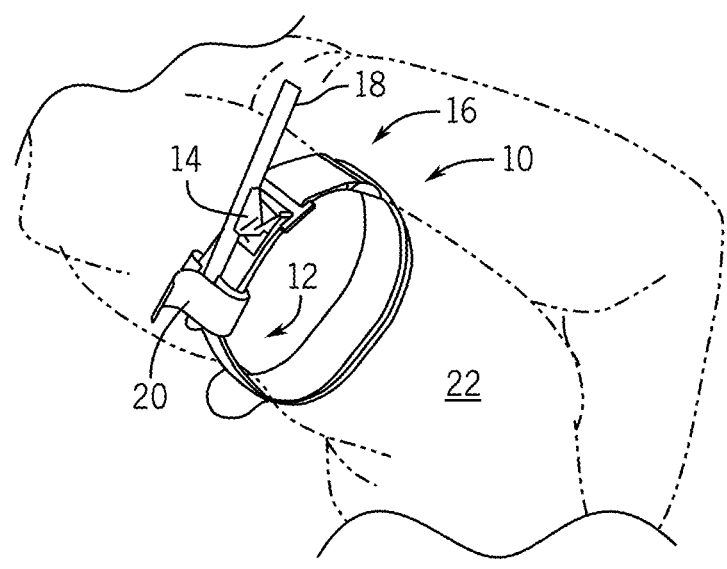
FIG. 1 is a perspective view of a traditional tourniquet deployed onto a limb.
Figure 2:
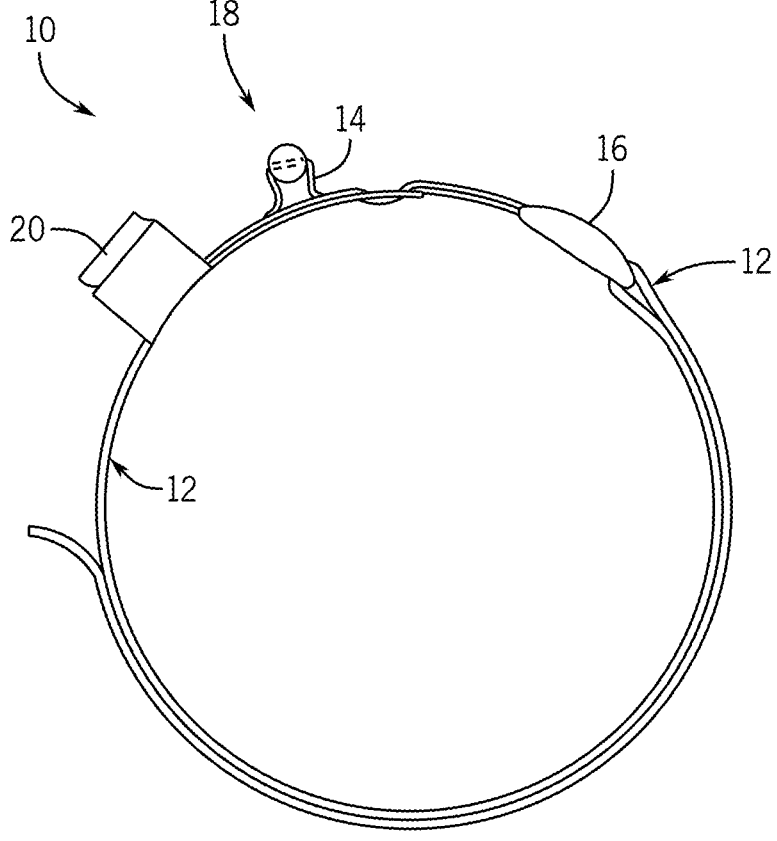
FIG. 2 is a plan view of the traditional tourniquet of FIG. 1.

Referring to FIGS. 1 and 2, a traditional tourniquet 10 is formed from a few standard components. The tourniquet 10 includes an outer sleeve 12, an inner strap 14, bulk tightening buckle 16, a fine tightening mechanism 18, and a locking system 20 for the fine tightening mechanism 18. As shown, the tourniquet 10 can be applied to an appendage or limb 22, in the illustrated example a leg of a person, and then tightened to restrict the flow of blood to the limb 22.

The outer sleeve 12 is a longitudinally extending material, for example, forming a belt-like structure designed to surround the limb 22. When the tourniquet 10 is applied to the limb 22, a first end of the outer sleeve 12 is looped through the buckle 16 and pulled tight around the appendage or limb 22, thus providing a means for circumferentially surrounding or encircling the limb 22. That is, to deploy the tourniquet 10 to the appendage or limb 22, a user wraps the tourniquet 10 around the limb 22, loops the outer sleeve 12 through the buckle 16, pulls the tourniquet 10 reasonably tight, and then folds or secures the outer sleeve back from the buckle 16 to lock the outer sleeve 12, as one would do with a belt.

With the tourniquet 10 engaged with the limb 22, the inner strap 14, which forms a length of inelastic binding strap or tape that extends from the outer sleeve 12 to the buckle 16, can be used to provide further, fine tightening of the tourniquet 10. Although a substantially non-elastic nylon binding strap type of material is preferred for use as the inner strap 14, other elongated types of materials may be used, such as a section of rope, belt, tubing, hose, band, or combinations thereof, where such structures thereby form a means for compressing a body part. The inner strap 14 is formed of a material that has frictional characteristics allowing it to slide relative to the outer sleeve 12 when a tensile force is applied to the inner strap 14. In this way, the inner strap 14 may be used to further tighten the tourniquet 10 using the fine tightening mechanism 18 that reduces the extending length of the inner strap 14 and tightens the tourniquet 10. For example, the fine tightening mechanism 18 may be rotated to cause the inner strap 14 to wrap about the fine tightening mechanism 18. Once sufficiently tightened, the tourniquet 10 may be secured by locking the fine tightening mechanism 18 using the locking system 20, which may form a strap or pocket that locks the fine tightening mechanism 18 in a particular position relative to the outer sleeve 12.

While the tourniquet 10 described above with respect to FIGS. 1 and 2 advantageously provides bulk and fine control and has been shown to serve as a suitably robust system for emergency field tourniquets, it is substantially limited by the shortcomings previously described. As such, the disclosure provides systems and methods for intelligent operation and/or control of a tourniquet system. As will be described, the systems and methods of the present disclosure may be adapted to be used with a traditional tourniquet system, such as the tourniquet system 10 described above with respect to FIGS. 1 and 2 or may be part of a new system. That is, as will be described, the systems and methods provided herein may be retrofitted or adapted for deployment with traditional tourniquet systems or may form part of a new system.

While the systems and methods are described herein with reference to the emergency windlass tourniquet of FIGS. 1 and 2, it should be noted that this is just one example of a "field tourniquet" and the systems and methods may be applicable to any type of field tourniquet with a strap and manually controllable tightening mechanism. This may include, but is not limited to, emergency tourniquets with windlass mechanisms, windlass and buckle mechanisms, clamp mechanisms, ratchet mechanisms, block and tackle mechanisms, cam mechanisms, elastic mechanisms, or others.

As will be described, the systems and methods provided herein may yield real-time feedback, guidance, and/or control. As some non-limiting examples, the systems and methods provided herein may integrate or retrofit force sensing and feedback systems with traditional tourniquets. Also, as a non-limiting example, the systems and methods provided herein may integrate or retrofit tissue oxygenation monitoring and/or feedback with traditional tourniquets. Alternatively, a new tourniquet system may be provided that facilitates the real-time monitoring of tissue oxygen and/or applied force. Whether retrofitted into existing systems or part of a new tourniquet system, the systems and methods provided herein facilitate real-time assessment of and achieving of adequate tourniquet deployment. Also, the systems and methods provided herein facilitate the tracking of limb viability for triage, even if patients are noncompliant or nonresponsive.

For example, in some non-limiting configurations, the present disclosure provides a portable, self-contained tissue oxygenation and/or force sensing toolkit that can be integrated with pre-existing, standard-of-care emergency tourniquets or assembled as a new tourniquet system. The toolkit can provide real-time monitoring of applied tourniquet pressure and/or tissue oxygenation along with tracking the time elapsed since a successful application. That is, monitoring tourniquet pressure can assist the user in reaching a threshold pressure required to restrict blood flow. Additionally, tissue oxygenation monitoring can assist the user by indicating successful arterial occlusion during tourniquet use as well as indicting limb health over time while the tourniquet is in use. For example, if the tourniquet is too tight or worn for too long, oxygen levels can decrease to critically low levels, endangering the ability to save the limb. The rate change of tissue oxygenation is another important variable that can be used to assess tissue viability. Furthermore, tracking time elapsed during tourniquet use can assist triage by lowering a risk of overuse. For example, even proper tourniquet use over extended periods of time can cause severe injury or limb loss and, therefore, elapsed time monitoring can reduce such risks. These and other capabilities of the present systems and methods are described in further detail below with respect to FIGS. 3-12.

Figure 3:
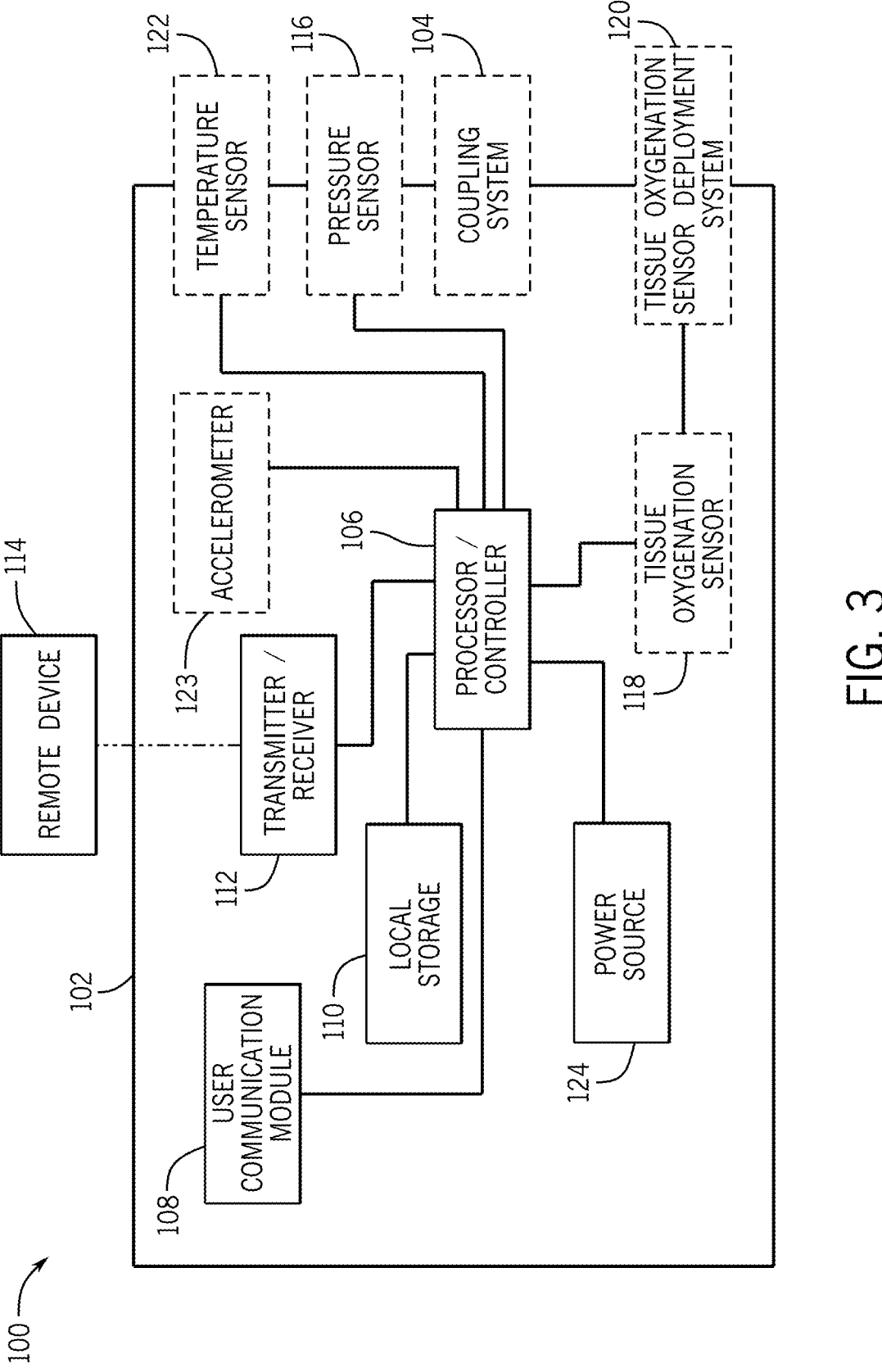
FIG. 3 is a schematic view of a system for tourniquet operation and control.

In particular, FIG. 3 illustrates a schematic layout of a system 100 according to some non-limiting configurations. As shown in FIG. 3, the system 100 can comprise a housing 102, a coupling system 104, a processor/controller 106, a user communication module 108, local storage 110, a transmitter/receiver 112, for example, configured to communicate with a remote device 114, a pressure sensor 116, a tissue oxygenation sensor 118, a tissue oxygenation sensor deployment system 120, a temperature sensor 122, an accelerometer 123, and a power source 124.

Generally, the housing 102 can house and protect electronics of the system 100. The coupling system 104 can couple the housing 102 to a tourniquet (such as the tourniquet 10 of FIGS. 1 and 2). The processor/controller 106 can control operations of the system 100, such as monitoring and analyzing patient parameters and communicating such parameters or other information to a user. The user communication module 108 can communicate such information to the user, for example, from a surface of the housing 102. The local storage 110 can store data, such as sensor data or other information, as well as processes to be executed by the processor/controller 106. The transmitter/receiver 112 can facilitate communication between the system 100 and the remote device 114, including data reporting, alerts, and/or instructions. The pressure sensor 116 can sense a measurement indicative of a pressure of the tourniquet around a limb. The tissue oxygenation sensor 118 can sense a measurement indicative of tissue oxygenation at the limb, and the tissue oxygenation sensor deployment system 120 can facilitate deployment of the tissue oxygenation sensor 120 in contact with the limb. The temperature sensor 122 can sense a measurement indicative of temperature at or adjacent the limb. The accelerometer 123 can sense a measurement indicative of movement of the housing 102 and, thus, the limb to which the tourniquet 10 is attached. The power source 124 can power the system 100.

Figure 4:
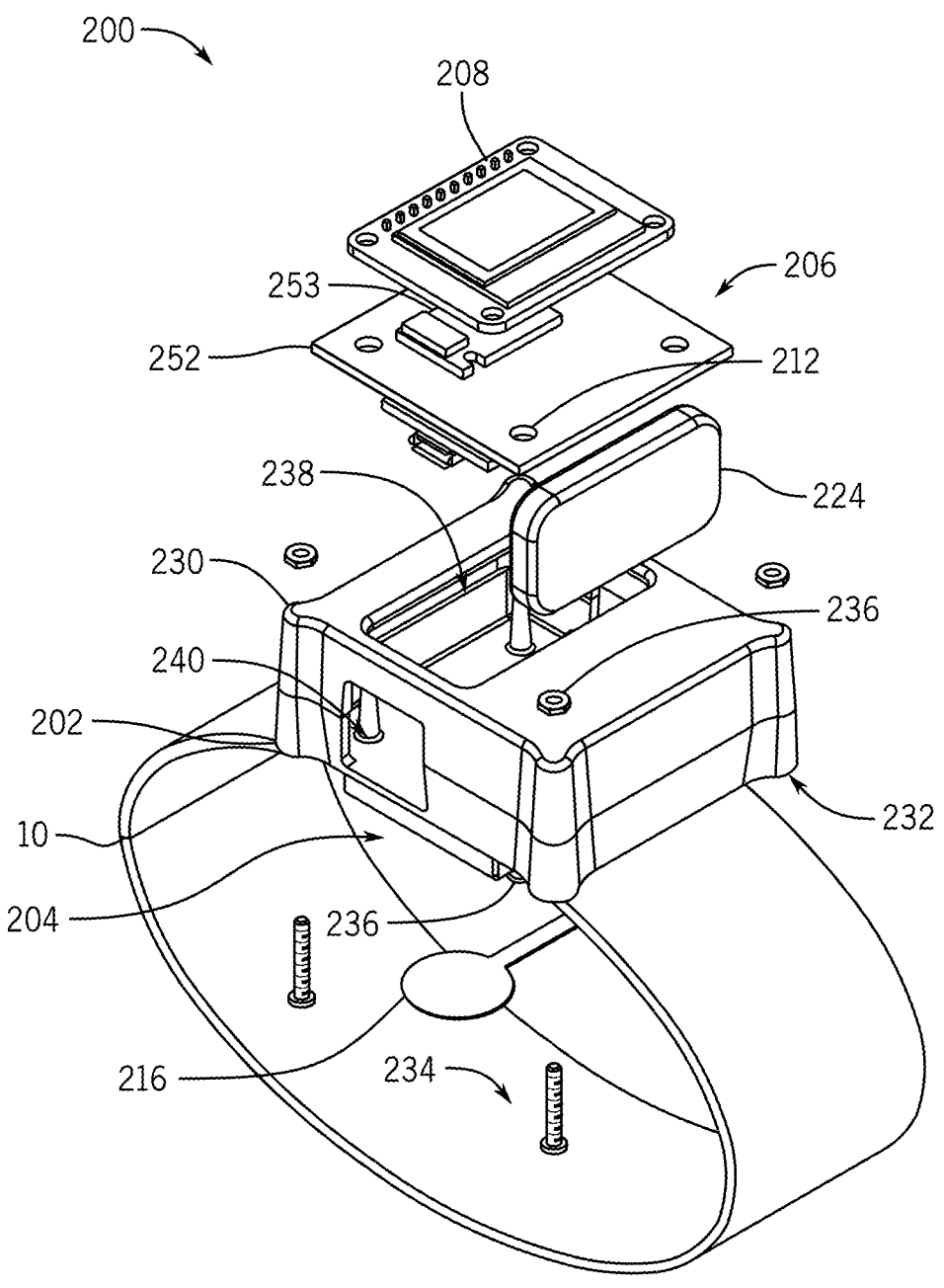
FIG. 4 is an exploded perspective view of a system for tourniquet operation and control.
Figure 5:
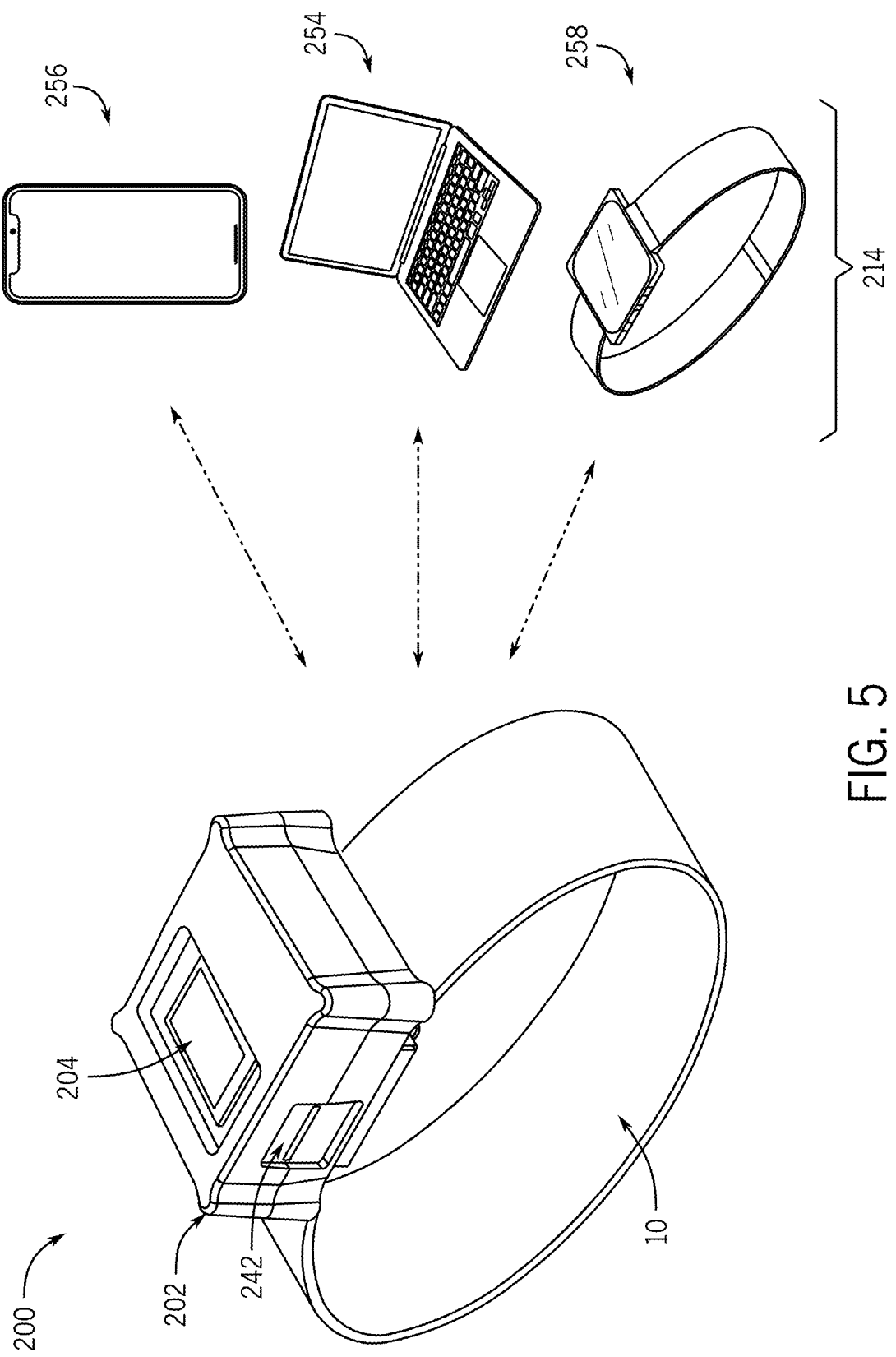
FIG. 5 is a perspective view of the system of FIG. 4.
Figure 6:
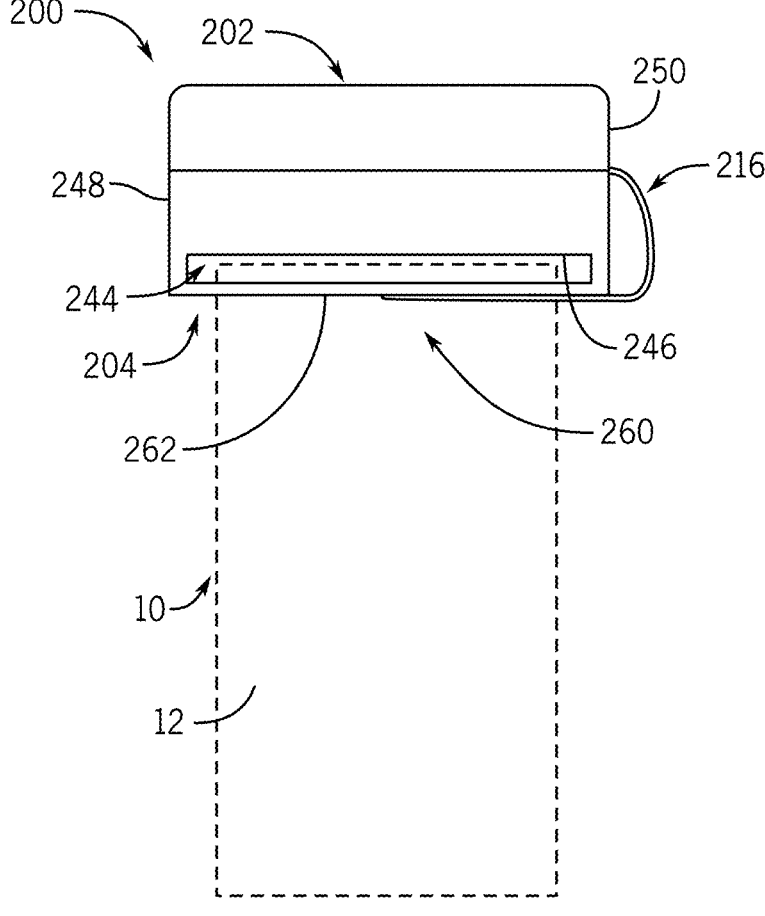
FIG. 6 is a side view of the system of FIG. 4.

More specifically, FIGS. 4-6 illustrate one non-limiting example of a system 200 coupled to a tourniquet 10 for use around a limb of a patient. As shown in FIG. 4, the system 200 includes a housing 202, a coupling system 204, a processor/controller 206, a user communication module 208, local storage (not shown), a transmitter/receiver 212, a pressure sensor 216, a tissue oxygenation sensor (not shown), a tissue oxygenation sensor deployment system 220 (shown in FIGS. 7A-7D), a temperature sensor (not shown), an accelerometer (not shown), and a power source 224. Notably, the system 200 may include similar components as the system 100, as described above and illustrated in FIG. 3, and, thus, such like components are numbered accordingly.

For example, the housing 202 can include an upper housing 230 and a lower housing 232 coupled together, such as by fasteners 234 and/or other mounting hardware 236, snap-fit connection, or other coupling methods. The housing 202 can include a first port window 238 to accommodate the user communication module 208, and a second port window 240 to accommodate, for example, a physical component, such as a communication port 242, of the transmitter/receiver 212. In some configurations, the housing 202, such as a connection point between the upper and lower housings as well as the port windows 238, 240, can include seal or coverings (not shown) to ensure that the housing 202 is substantially water proof or water resistant in order to protect the electronics housed therewithin from liquids, dirt, and/or other contaminants. Furthermore, in some configurations, the housing 202 can comprise a lightweight photopolymer resin, for example, constructed via 3D printing. In another non-limiting configuration, the housing 202 can comprise a lightweight polymer formed by injection molding, extrusion, or similar plastic manufacturing methods. In yet another non-limiting configuration, the housing 202 can be fabricated through machining such as milling or turning. The flexibility of such material can allow for proper ingress protection and impact resistance ratings suitable for repeated use of the system 200. In another non-limiting configuration, the housing 202 can comprise padding or other similar shock-absorbing material or component intended to protect the internal components from mechanical shocks or impact. As shown in FIGS. 4-6, in some configurations, housing 202 can also comprise rounded edges.

Thus, generally in some configurations, the housing 202 can be at least water resistant, and can further be shock proof for use in wet or rainy environments, and substantially rugged for increased durability in the field. The housing 202 can also be configured for substantial ruggedness against humidity and vibration in some configurations.

The coupling system 204 can be coupled, directly, integrally, or indirectly, to the housing 202 and can removably engage the tourniquet 10. As a result, the coupling system 204 enables the system 200 to be retrofitted onto any traditional tourniquet. Accordingly, the system 200 may be adaptable to integrate onto any pre-existing emergency tourniquet and, thus, can facilitate proper tourniquet application on a patient in any environment regardless of the tourniquet available. However, in some applications, the system 200 may be manufactured into and/or supplied with a new tourniquet (e.g., to be sold as a complete tourniquet/monitoring system).

Additionally, as the coupling system 204 serves as another structural component of the system 200, in some applications, can be considered part of the housing 202. In some configurations, the coupling system 204 can comprise a lightweight photopolymer resin, such as the same material as the housing 202. In another non-limiting configuration, the coupling system 204 can comprise a polymer formed by injection molding, extrusion, or similar plastic manufacturing methods. In yet another non-limiting configuration, the coupling system 204 can be fabricated through machining such as milling or turning. The flexibility of such materials can allow for the benefits described above and can further allow the coupling system 204 to conform to the curvature of the limb during tourniquet application. Furthermore, in some configurations, the entire system 200 (including the housing 202 and the coupling system 204) can be small enough to not interfere with proper tourniquet application, while permitting a large enough surface for the user communication module 208 to provide easy readability of information to the user. In one configuration, total dimensions of the system 200 can be less than 70×70×70 mm^3 and the system 200 can weigh less than 100 grams.

Referring back to the coupling system 204, to engage the tourniquet 10, the coupling system 204 can be structured to define a mounting passage 244, as shown in FIG. 6. More specifically, the mounting passage 244 can be configured to receive the tourniquet 10 to secure the housing 202 to the tourniquet 10 and arrange the pressure sensor 216 between the tourniquet 10 and the patient. More specifically, when deploying the system 200, an outer sleeve 12 of the tourniquet 10 can be fed through or positioned within the mounting passage 244. As a result, while the housing 202 can remain substantially above the tourniquet 10 (i.e., distal from the patient), the coupling system 204 can be positioned between the tourniquet 10 and the patient.

Generally, the coupling system 204 can be designed to clip-on or slide-on to any currently existing strap-based emergency tourniquet. More specifically, in some configurations, as shown in FIG. 6 the coupling system 204 is a u-shaped structure coupled to a lower surface 246 of the housing 202 at left and right sides thereof, thus defining the mounting passage 244 extending from front to back of the housing 202. In some configurations, the u-shaped structure can be integrally coupled to the left and right sides of the lower surface 246 so that the sleeve 12 of a tourniquet 10 can be slid through the mounting passage 244, thereby coupling the system 200 to the tourniquet 10. In other configurations, the u-shaped structure can be removably and/or hingedly coupled to the left and/or right sides of the lower surface 246 so that the u-shaped structure can be clipped around the strap 12 of a tourniquet 10, thereby coupling the system 200 to the tourniquet 10. Furthermore, while the u-shaped structure is described as being coupled to left and right sides of the lower surface 246 of the housing 202, in some configurations, the u-shaped structure can instead be coupled to left and right side surfaces 248, 250 of the housing 202 or extend directly down from left and right side surfaces 248, 250 of the housing 202.

Accordingly, the housing 202 can make the system 200 a small, portable device, while the processor/controller 206 can allow the system 200 to be self-contained by providing data processing capabilities. For example, the processor/controller 206 can include, for example, a circuit board 252 housing one or more microcontrollers in communication with one or more components of the system 200. The circuit board 252 can be positioned within the housing 202, for example, via the fasteners 234 and/or mounting hardware 236 used to couple together the housing 202. In one example, the processor/controller 206 further includes a bus 253 (such as an I2C bus) for communication between components housed on the circuit board 252 and/or connected to the processor/controller 206. The processor/controller 206 can thus communicate (e.g., via the bus 253), with the user communication module 208, local storage (e.g., internal memory), the transmitter/receiver 212, the pressure sensor 216, the temperature sensor, and/or the tissue oxygenation sensor, among other components. Generally, the processor/controller 206 can operate in conjunction with these components to record measurements indicative of pressure, temperature, tissue oxygenation, and/or time; locally store the measurements; analyze the measurements; and/or communicate the measurements, alerts, and/or reports to one or more users locally and/or remotely.

That is, generally, the processor/controller 206 can receive feedback from any of the above components and communicate at least one output signal to the user via the user communication module 208. For example, as shown in FIGS. 4 and 5, the user communication module 208 of the system 200 can include a screen configured to display information (e.g., a "user report" generated by the processor/controller 206) locally to the patient or a user (such as triage personnel), as controlled by the processor/controller 206. Such information can include, but is not limited to, an insufficient tightening pressure alert, a proper tightening pressure alert, a retightening alert, a desired oxygenation alert, an insufficient oxygenation alert, a time elapsed or countdown, an extended time warning, an extending time alert, an in-use alert, sensor measurements or other processed data, and/or patient parameters. Such information can also include instructions to the user, such as the steps to apply the tourniquet, step-by-step instructions that may be provided based on information gleaned from the sensors, and/or next-step actions. As a result, the information can provide real-time feedback to allow both trained and untrained first-responders to effectively apply tourniquets under less than ideal conditions, while keeping track of tourniquet application times for triage, even if the patient is noncompliant or nonresponsive.

For example, an insufficient tightening pressure alert can indicate, to the patient or the user, that the tourniquet is insufficiently tightened, such as below a low pressure threshold, above a high pressure threshold, and/or outside of a desired pressure range, as determined by the processor/controller 206 based on feedback from the pressure sensor 216. In contrast, a proper tightening pressure alert can indicate that the tourniquet is properly tightened, such as above the low pressure threshold, below the high pressure threshold, and/or within the desired pressure range based on feedback from the pressure sensor 216. The retightening alert can indicate that the tourniquet needs retightening, for example, if pressure moves from within the desired range to below the low pressure threshold. The desired oxygenation alert can indicate that tissue oxygenation is above a low threshold, within a desired range, and/or a rate of change of tissue oxygenation meets a desired metric, as determined by the processor/controller 206 based on feedback from the tissue oxygenation sensor. In contrast, an insufficient oxygenation alert can indicate that tissue oxygenation is below a low threshold, outside a desired range, and/or the rate of change of tissue oxygenation falls outside a desired metric, based on feedback from the tissue oxygenation sensor.

Referring to timing information communicated via the user communication module 208, the time elapsed or countdown can indicate the actual time elapsed once proper tightening pressure has been determined, or a countdown from a threshold number once proper tightening pressure has been determined, as determined by the processor/controller 206 based on an internal clock and feedback from the pressure sensor 216 and/or the tissue oxygenation sensor. The threshold number may be a desired maximum tourniquet time such as, for example, a time between 4-5 hours, inclusive. The extended time warning can indicate when the elapsed time or countdown reaches a first threshold within the desired maximum tourniquet time (for example, at a time between 5-7 hours, inclusive, or another time). The extended time alert can indicate when the elapsed time or countdown reaches a second threshold within the desired maximum tourniquet time, after the extended time warning (for example, a time between 5.5-7.5 hours, inclusive, or another time).

Regarding additional information communicated via the user communication module 208, an in-use alert can indicate that the tourniquet is in use. The data measurements can indicate measurements (e.g., raw or processed measurements), such as pressure, temperature, motion, and/or tissue oxygenation, based on feedback from the pressure sensor 216, the temperature sensor, the accelerometer, and/or the tissue oxygenation sensor. The patient parameters can indicate one or more parameters specific to the patient, for example, if those were communicated to the processor/controller 206 before or during tourniquet application.

It should be noted that not all of the alerts, warnings, or information described above may be communicated to the user via the user communication module 208. For example, in some configurations, only a sufficient tightening pressure alert, a pressure measurement, and a timer is communicated. In particular, while the system 200 may be capable of measuring and processing multiple parameters that are not directly relevant to the end-user, only that information that is very important for the end user can be clearly displayed in a manner so that bleeding control can be achieved intuitively, quickly, and efficiently without any potential confusion even for first time users who have no prior-experience, Of course, other combinations of alerts, warnings, and information may also be contemplated in some configurations.

With further reference to the user communication module 208, the screen can be an LED or OLED screen that communicates text and/or images. For example, the screen can present a current pressure measurement in real time, a current tissue oxygenation measurement in real time, a timer, and/or other text. The screen can further present graphics or symbols for certain alerts, such as a "thumbs up" signal as the proper tightening pressure alert, a "thumbs down" signal as the insufficient tightening pressure alert, and/or an indicator dial moving between insufficient and sufficient pressure indications based on measured pressure. In some applications, the screen can further be backlit to be viewed in the dark. Alternatively, in some applications, the screen can be an "e-ink" display, which can be easily readable under most lighting conditions and has low energy consumption.

Furthermore, in addition or alternatively, the user communication module 208 can include one or more LEDs to communicate any of the above information. In one example, the user communication module 208 can include one or more red/green light indicators, where a red LED is lit to communicate the insufficient tightening pressure alert and a green LED is lit to communicate the proper tightening pressure alert. In another example, a multi-color LED with a red-to-green light transition spectrum can communicate both insufficient tightening pressure and proper tightening pressure (e.g., moving from red to green as pressure reaches the desired range). In yet another example, a multi-color LED with a red-to-white-to-blue light transition spectrum can communicate both insufficient, under-tightening pressure (below a pressure threshold) in the red spectrum, proper tightening pressure in the white spectrum, and insufficient, over-tightening pressure (above a pressure threshold) in the blue spectrum. In yet another example, an LED can flash to communicate the extended time alert and/or the extended time warning (such as flash at one rate to communicate the extended time alert and flash at a second, faster rate to communicate the extended time warning). Other colors, alert types, and ranges may also be contemplated in some applications.

In addition or alternative to the visual communication modules (e.g., the screen and/or LEDs), the user communication module 208 can also include an audio communication module configured to communicate the information via an audible indication, such as a series of beeps or sounds. As such, the system 200 can include, for example, a speaker or other audio mechanism (not shown) in communication with the processor/controller 206 to serve as the audio communication module. In one non-limiting example, the audio communication module can beep to communicate the extended time alert or the extended time warning (such as beep at one rate to communicate the extended time alert and beep at a second, faster rate to communicate the extended time warning). In another non-limiting example, the audio communication module can communicate instructions to the user for the placement and tightening of the tourniquet, and could provide audio information informed by the sensors described herein.

Also, in some configurations, user communication module 208 can include a tactile communication module configured to communicate the information via a series of vibrations. In some configurations, the processor/controller 206 can be programmed to communicate via the visual communication module, the audio communication module, the tactile communication module, or some combination thereof, for example, based on the external environment or user preference. For example, in public mass-casualty environments, audio communication may be desired, whereas in battlefield or other stealth environments, audio communication may not be desired.

Furthermore, while the user communication module 208 has been described so far as passively providing communication to the user, in some configurations, the user communication module 208 can include one or more user inputs for the user to communicate information to the processor/controller 206 and/or to receive information from the processor/controller 206 via active interaction therewith. For example, in some configurations, the housing 202 can include one or more buttons, keys, switches, or the like (not shown), as user inputs. Via the user inputs, the user or patient can turn on the system 200 (e.g., via a power or on/off button), provide patient information (such as, but not limited to, patient size, sex, limb type, limb circumference, blood pressure, optimal pressure thresholds, optimal tourniquet wear time, etc.), reset the system (e.g., to restart the timer), switch between communication modules (e.g., audio, visual, tactile, or a combination thereof), provide other inputs, or request information, such as measurements or other data. For example, implementing a power button can help save battery life of the system 200. Alternatively, the system 200 may include a stand-by or low-battery mode until certain sensors are activated or other inputs are provided, or may include an insulating pull-tab to prevent the power source 224 from energizing prior to use. In another example, patient information above related to the patient's specific physiology (e.g., blood pressure, limb circumference) can be provided to customize thresholds and alerts individualized to the patient. Such information may be programmed into the system 200 in advance (e.g., to "preset" the system 200 to the individual) or at the time of tourniquet application via the user communication module 208 (or via a remote device 214, as described below).

Local storage can refer to memory within the system 200 (e.g., housed on the circuit board 252) and can include programs and/or algorithms for execution by the processor/controller 206. Furthermore, the processor/controller 206 can store raw data from the sensors, processed measurements, analyses, and/or other information locally via the local storage. For example, in some applications, the processor/controller 206 can store a data log of a tourniquet use session, including a time at which the tourniquet pressure is properly applied, periodic pressure, temperature, and/or tissue oxygenation measurements, times at which one or more alerts are communicated, and/or other information. If the reset button is pressed by the user, the processor/controller 206 can start logging a new tourniquet use session. In a non-limiting example, the local storage can further be used to store individual physiological parameters that can be used in the interpretation of the sensor data (e.g., to customize thresholds to the patient). For example, a patient's baseline systolic blood pressure could be stored in the device and used to set the circumferential pressure levels for tourniquet tightening.

While the system 200 can locally store information, the system 200 can further communicate information (e.g., by generation of one or more "user reports") to one or more remote devices 214 via the transmitter/receiver 212. The transmitter/receiver 212 can include a wireless communication module configured to communicate to a remote device 214 via cellular, WiFi, Bluetooth, or other proprietary wireless transmission protocols. In one non-limiting example, the wireless communication module can be a WiFi IoT device deployed on the circuit board 252 to provide communication via WiFi-based mesh networks. In another non-limiting example, the wireless communication module can include one or more wireless transmitters configured to provide Bluetooth connections within a specified range (e.g., 100-300 feet, or another range). In yet other non-limiting examples, the wireless communication module can include long range or other sub-GHz radio transmitters configured to connect devices across long ranges (in the range of kilometers) with relatively low power consumption.

In addition or alternatively, the transmitter/receiver 212 can include a wired communication module configured to communicate to the remote device 214 via a plug-in. For example, as shown in FIGS. 4 and 5 and noted above, the housing 202 can include a second port window 240 to accommodate a physical component of the wired communication module. In this example, the physical component can be a communication port 242, such as a USB port, coupled to the circuit board 252. However, other communication ports may also be contemplated. A user can plug a remote device 214 into the system 200 via the communication port 242 in order to retrieve information in real-time, retrieve information that was previously stored in local storage, communicate information to the processor/controller 206, such as patient information or programming instructions, etc. In some configurations, the second port window 240 can include a sealed covering (such as a waterproof plug) in order to protect the port 240 from water, blood, dirt, or other contaminants.

Thus, the system 200 can be configured to communicate in real-time and/or retrospectively, wired and/or wirelessly, with a remote device 214. A remote device 214 can be, but is not limited to, an external computer 254 (shown in FIG. 5), a server, a mobile device 256, a tablet, a wearable device 258, cloud storage, or any other suitable communication partner. For example, a tourniquet 10 may be applied using the system 200 in the field, with the processor/controller 206 logging the tourniquet use session and storing the session to local storage. Once the patient is transferred to a hospital, the tourniquet use session data can be downloaded, via the transmitter/receiver 212, from the local storage to a hospital server, hospital computer 254, caretaker mobile phone 256, or other remote device 214 in order for hospital personnel to better triage the patient. In a traumatic injury scenario where the user applying the tourniquet is not providing definitive care, the recording functionality of the system 200 enables the processor/controller 206 to report information to downstream healthcare providers on the state of the occluded limb. Such information, for example, can include a record of the tourniquet's tension over time along with the duration of tourniquet application.

In another remote device example, a tourniquet 10 may be applied using the system 200 in the field, and measurements, alerts, and/or other information can be transmitted in real-time to a user's mobile phone 256, tablet, or wearable device 258 (such as a smart watch). In a situation where multiple tourniquets must be deployed to multiple patients, the user's remote device 214 can serve as a central hub receiving information from the multiple systems 200 to better triage the patients (e.g., understanding which patients need more immediate care, such as tourniquet retightening, or soonest transfer to health care personnel for definitive care based on estimated time left before an ischemic event, etc.).

The pressure sensor 216 can be in communication with the processor/controller 206 and can be configured to sense a measurement indicative of pressure being applied to the limb when the tourniquet 10 is tightened around the limb, that is, during application and continued wear. In other words, the pressure sensor 216 can provide measurements to the processor/controller 206 indicative of a pressure being applied by the tourniquet 10. Based on these measurements, the processor/controller 206 can determine whether the tourniquet 10 is sufficiently tightened around the limb and start the timer/countdown; and send a proper tightening pressure alert, an insufficient tightening alert, a tightening alert, an extended time warning, or an extended time alert.

The tourniquet 10 can be properly tightened when the measured pressure reaches a minimum threshold pressure. This minimum pressure can be, for example, a pressure necessary for occlusion to sufficiently stop or hinder bleeding. The minimum threshold can be a static number stored in the local storage (for example, 250 mm Hg, or another number), may include a plurality of numbers along a curve and selected by the processor/controller 206 based on patient information provided to the processor/controller 206 (such as limb type, limb circumference, patient sex, patient size, etc.), and/or may include a varying number based on data learned over time by the processor/controller 206. Additionally, as a tourniquet 10 may loosen over time during application (e.g., depending on strap type or dynamic physiological changes during trauma), pressure falling back below the minimum threshold may indicate that retightening is necessary. Additionally, in some configurations, the tourniquet can further be sufficiently tightened when the measured pressure is maintained below a maximum threshold pressure. The maximum pressure can be, for example, a pressure that could potentially completely occlude blood flow through the limb.

That is, while under-tightening can lead to continued hemorrhage, over-tightening can lead to poor circulation, ischemia, and/or tissue necrosis. Furthermore, when the tourniquet is sufficiently tightened, or over-tightened, for an extended period of time, such prolonged use may lead to additional injuries or compartment syndrome. Thus, generally, the processor/controller 206 can communicate: properly tightening pressure alerts when the applied pressure is within a desired range (i.e., above the minimum threshold and below the maximum threshold); insufficient tightening alerts when the applied pressure is outside the desired range; retightening alerts when the applied pressure falls below the minimum threshold; and extended time warnings or extended time alerts when pressure within the desired range is applied for an extended period of time.

In some configurations, the pressure sensor 216 can include a sensing surface 260 positioned adjacent the limb when the system 200 is deployed, for example, along a bottom surface 262 of the coupling system 204, as shown in FIG. 6. As a result, when the tourniquet is deployed, the pressure sensor 216 can sense a compressive force between the tourniquet and the limb. More specifically, as shown in FIG. 6, the pressure sensor 216 may be coupled to the processor/controller 206, for example, attached to the circuit board 252 within the housing 202, extend out of the housing 202, and loop around to the bottom surface 262 of the coupling system 204. The pressure sensor 216 can be coupled to the bottom surface 262 via a suitable adhesive or other mechanical coupling methods. In other configurations, as further described below with respect to FIGS. 8-11, the pressure sensor 216 may be enclosed or covered within the coupling system 204 rather than exposed along the bottom surface 262.

Furthermore, in some configurations, the pressure sensor 216 can be a thin-film capacitive force sensor. For example, as the user tightens the tourniquet 10, the capacitive force sensor makes contact with the limb and compresses. In turn, the capacitive force sensor generates a change in electrical signal depending on the amount of pressure being applied, which is then communicated to the processor/controller 206. A pre-generated calibration curve can be stored in the local storage, and the processor/controller 206 can process the electric signals in real-time to convert them to pressure or force measurements. In other configurations, the pressure sensor 216 can be a resistive force sensor configured to be compressed and provide force signals to the processor/controller 206. Though, it should be noted that, in some applications, capacitive force sensors may provide better sensitivity and repeatability compared to resistive force sensors. Furthermore, in yet other configurations, the pressure sensor 216 can be a mechanical pressure sensor 216 and/or measure force via a combination of methods.

The tissue oxygenation sensor can be in communication with the processor/controller 206 and can be configured to measure the limb's tissue oxygenation during tourniquet application. Based on these measurements, the processor/controller 206 can determine successful arterial occlusion and measure limb health while the tourniquet 10 is worn. Also, based on tissue oxygenation measurements, the processor/controller 206 can send a desired oxygenation alert or an insufficient oxygenation alert. For example, if the tourniquet is too tight or worn for too long, oxygen levels can decrease to critically low levels, and resulting ischemic events can endanger the ability to save the limb and/or increase a risk of cytotoxicity once the tourniquet 10 is removed. Accordingly, the processor/controller 206 can communicate a desired oxygenation alert or an insufficient oxygenation alert when the tissue oxygenation is above or below a threshold level, respectively.

Furthermore, based on tissue oxygenation measurements, the processor/controller 206 can adjust the countdown timer. For example, the processor/controller 206 can monitor tissue oxygenation over time, where a significant rate of change over time (such as a quick drop in oxygen levels) can affect the estimated time left before an ischemic event. Accordingly, in one non-limiting example, the processor/controller 206 can communicate an alert or adjust a countdown timer when a change in a rate of change of tissue oxygenation measurements rises above threshold level.

In some configurations, the tissue oxygenation sensor can be a spectroscopic sensor that utilizes optical spectroscopy to measure tissue oxygenation. In other non-limiting configurations, the tissue oxygen sensor can be a lifetime sensor that utilizes phosphorescence lifetime spectroscopy to measure tissue oxygenation (for example, rather than physically measuring a spectrum, measuring an intensity over time). In yet other non-limiting configurations, the tissue oxygen sensor can be an array of sensors, such a CCD, CMOS, photodiode array or combination thereof. As such, the tissue oxygenation sensor(s) can be positioned to be in close tissue contact when the tourniquet 10 is applied in order to measure tissue oxygenation. Accordingly, the oxygenation sensor deployment system 220 can accomplish proper tissue contact for oxygenation sensing. For example, in one configuration, the tissue oxygenation sensor may be integrated into a transdermal pad (not shown) configured to be in contact with the user's skin when the tourniquet is deployed. The transdermal pad can be deployed along the bottom surface 262 of the coupling system 204, for example, adjacent to or substantially surrounding the pressure sensor 216. One non-limiting example of this configuration is described in U.S. Pat. No. 10,016,164, the entire contents of which is incorporated herein by reference.

FIGS. 7A-7D illustrate other non-limiting examples of the tissue oxygenation sensor deployment system 220 in the form of a microneedle array 264 in a block 266. More specifically, the tissue oxygenation sensor can include one or more spectroscopic sensors or lifetime sensors embedded into an array of microneedles 264 configured to penetrate the user's tissue when the tourniquet 10 is deployed. For example, the tissue oxygenation sensor may include a single sensor coupled to multiple microneedles, or a plurality of sensors each coupled to a microneedle. As such, the array of microneedles can extend the spectroscopic sensors or lifetime sensors into the user's tissue. Thus, the deployment system 220 can include the block 266 that houses the microneedle array 264 and is part of or coupled to the bottom surface 262 of the coupling system 204. The block 266 and the microneedle array 264 can be deployed along the bottom surface 262 of the coupling system 204, for example, adjacent to or substantially surrounding the pressure sensor 216. In one example, the microneedle array 264 can be a 10×10 array of microneedles sized between 25-100 mm^2.

Figure 7A:
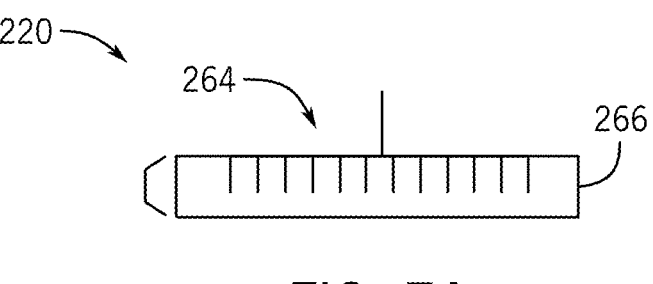
FIGS. 7A-7F are side views of a tissue oxygenation sensor deployment system for use with the system of FIG. 4, where
Figure 7B:
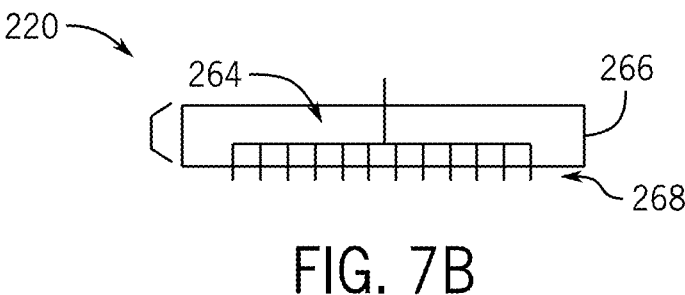
Figure 7C:
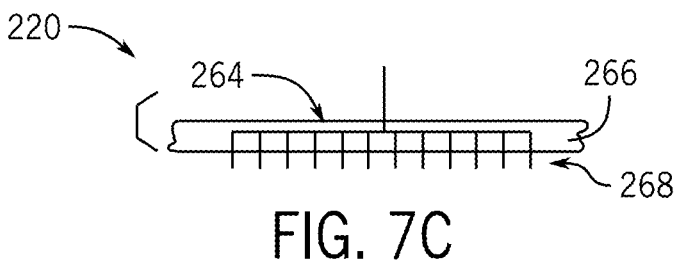
Figure 7D:
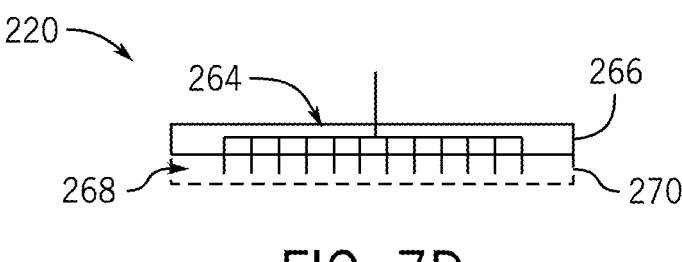

Generally, the block 266 can be configured to sufficiently cover or protect microneedle tips 268 when the tourniquet 10 is not deployed, as shown in FIG. 7A, but permit the microneedle tips 268 to extend out of the block 266 and puncture the patient's tissue when the tourniquet 10 is tightened. In some configurations, as shown in FIG. 7B, the block 266 can comprise a material, such as foam, that permits the needle array 264 to be pushed through the block 266 until the needle tips 268 extend out of the block 266 (e.g., via a plunger mechanism, not shown). In another configuration, as shown in FIG. 7C, the block 266 can comprise a material, such as foam, that is compressed while the tourniquet 10 is tightened, thus permitting the needle tips 268 to extend out of the block 266. In yet another configuration, as shown in FIG. 7D, the block 266 can comprise a lower membrane 270 configured to rip off the block 266 upon experiencing a certain pressure, thus exposing the needle tips 268.

Figure 7E:
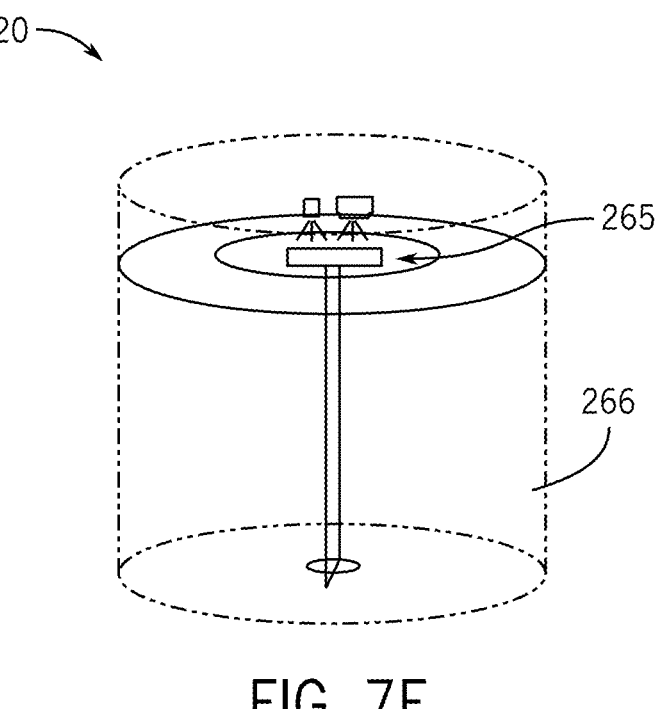
Figure 7F:
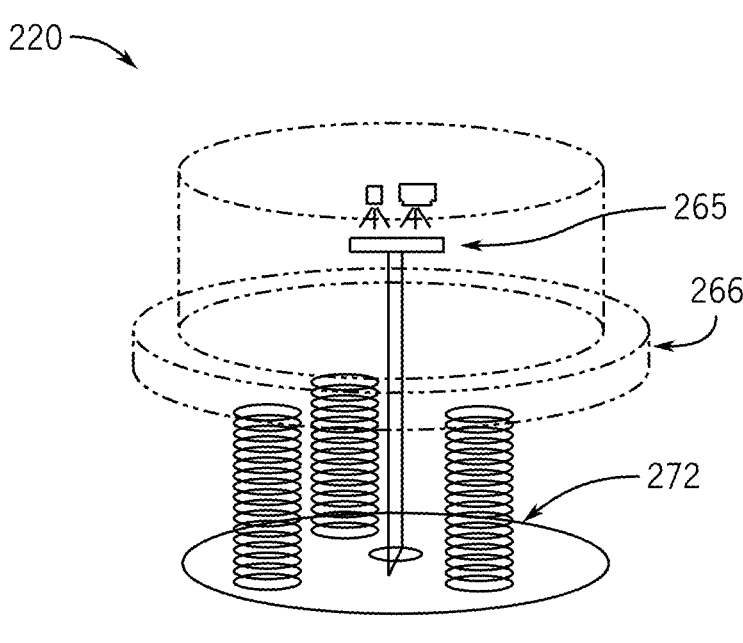
Figures 8, 9:
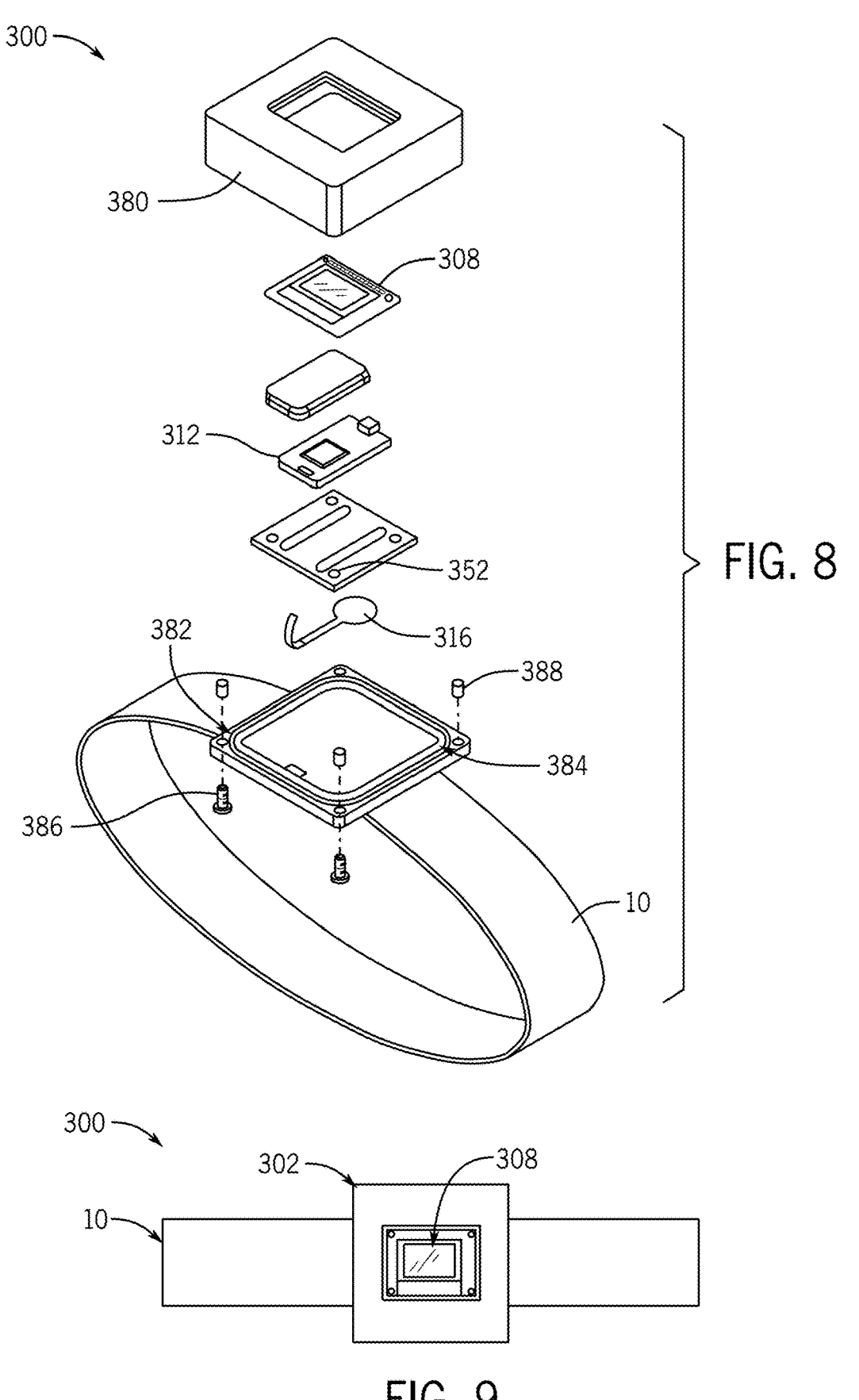
FIG. 8 is an exploded perspective view of another system for tourniquet operation and control.
FIG. 9 is a top-down view of the system of FIG. 8.
Figure 10:
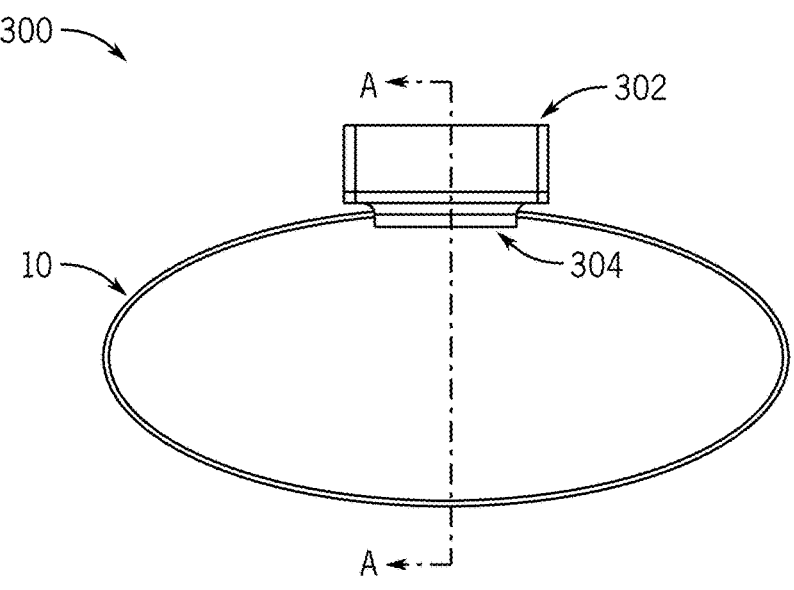
FIG. 10 is a plan view of the system of FIG. 8.

FIGS. 7E and 7F illustrate further configurations, where FIG. 7E shows a single needle unit 265 in a block 266 of compressible material (e.g., compressed under a desired force). FIG. 7F shows a single needle unit 265 in a block 266 that comprises a compressible structure, such as a 3D printed structure with a carton or springs 272 that compresses under a desired force.

In yet another example, the tissue oxygenation sensor can be embedded into an array of needles configured to penetrate the user's tissue when the tourniquet 10 is deployed. The needle array may take the same forms as the various examples of microneedle arrays 264 and/or blocks 266 described above, though with larger needles having optical sensors embedded therein. Similarly, the needle array can be deployed along the bottom surface 262 of the coupling system 204, for example, adjacent to or substantially surrounding the pressure sensor 216. The larger needles of the needle array may be able to penetrate one or more layers of clothing, for example, so that the system 200 may not require direct skin contact for tissue penetration. Additionally, in some configurations, to accommodate shear stresses associated with tourniquet tightening, the individual needles may be deployed to pivot, such as on ball pivots.

Figure 13:
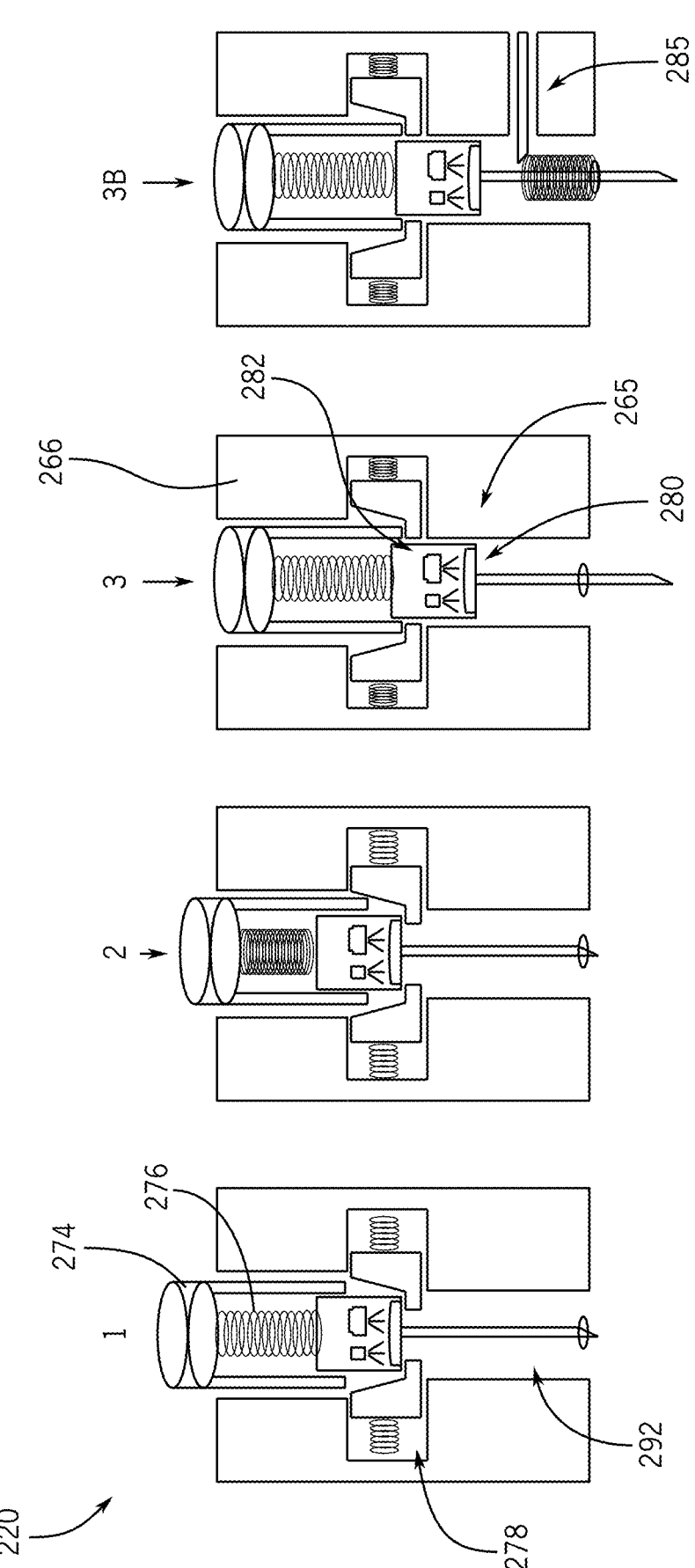
FIG. 13 is a series of side views of a tissue oxygenation sensor deployment system for use with the system of FIG. 4, from an undeployed to a deployed state.

FIG. 13 illustrates an example deployment system 220 for use with the one or more needle units 265 (e.g., of a single microneedle system, microneedle array 264, a single needle system or a needle array). Generally, the deployment system 220 includes a button 274 connected over a spring 276, and one or more spring-activated blocks 278, along with block material 266, as described above.

As shown in FIG. 13, the button 274 can contact the needle unit 265 via the spring 276 so that, when the button 275 is pushed down (e.g., by experiencing a threshold force, such as 250 mmHg, from a tourniquet tightening around a limb), the needle unit 265 is, in turn, pressed downward. The needle unit 265 can then pierce through the block 266, as with the configurations illustrated in FIGS. 7A-7F, or can extend through an aperture 292 of the block 266, as shown in FIG. 13. In the configuration of FIG. 13, then, the block 266 may not need to be compressible material. The spring-activated blocks 278 can hold the needle unit 265 in an undeployed state until the force of the button 274 and spring 176 causes the needle unit 265 to press the blocks 278 outward, overcoming the hold strength of the blocks 278. In this manner, the blocks 278 can include angled sides and/or a shoulder portion to initially hold the needle unit 265 in place. Additionally, in some configurations, a spring-activated system 285 or other mechanical method can be used to retract the needle unit 265 from the tissue, counteracting the forces of the spring 276.

Furthermore, with respect to the needle unit 265, as shown in FIG. 13, the needle unit 265 can include an oxygen sensing layer 280 and optoelectronics 282 configured to provide an oxygen sensor readout.

Figure 14:
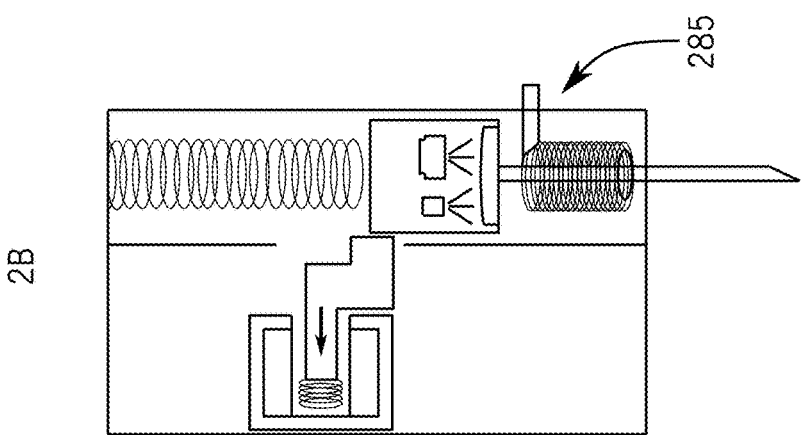
FIG. 14 is a series of side views of another tissue oxygenation sensor deployment system for user with the system of FIG. 4, in an undeployed and a deployed state.
Figure 14:
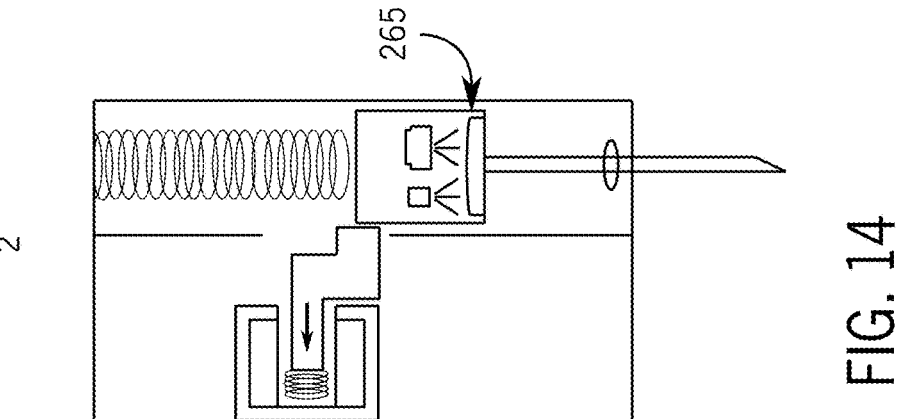
Figure 14:
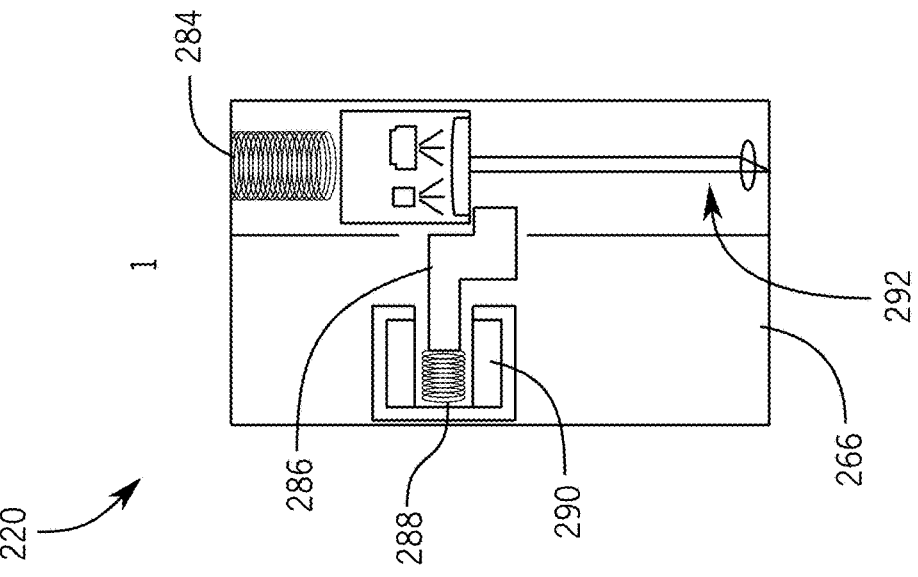

FIG. 14 illustrates another example deployment system 220 for use with a needle unit 265. Generally, the deployment system 200 can include a spring 284 and a plunger 286, along with block material 266, as described above. The plunger 286 can be pushed towards the needle unit 265 by a spring 288 and is mounted in a linear solenoid construction. The plunger 286 is surrounded by coil windings and a case or frame 290 where electrical connections are placed. The controller/processor 206 can pass an electrical signal to the case/frame 290 when the tourniquet reaches a desired pressure (e.g., 250 mm Hg), and a current will flow and induce a magnetic field in the coil. In turn, the magnetic field will retract the plunger 286 and release the needle unit 265. The spring 284 can initially be preloaded (that is, held in a retracted state) via the plunger 286 so that, when the plunger 286 is retracted, the spring 284 will be released to expand and push the needle unit 265 downward through the block material 266. Alternatively, the spring 284 can be loaded by a mechanical button (not shown), such as the button 274 described above with respect to FIG. 13. Additionally, in some configurations, a spring-activated system 285 or other mechanical method can be used to retract the needle unit 265 from the tissue, counteracting the forces of the spring 284.

Notably, both deployment system constructions described above with respect for FIGS. 13 and 14 are only triggered when the tourniquet applied force is above a certain threshold. This can ensure that the needle unit 265 will not experience shear forces when the tourniquet is still being tightened. Additionally, to make both designs mechanically more stable against forces from outside when, for example, the housing 102 is dropped on the floor, a mechanical pin or lever (not shown) can also be incorporated, which would have to be manually removed before the needle unit 265 can be triggered.

Additionally, while tissue oxygenation sensing is described above with respect to optical sensing via transdermal pads or needle designs (e.g., via oxygen sensing porphyrins), other configurations may instead include blood flow sensing, oxygen saturation monitoring, or other methods to provide an indirect metric of bleeding control.

As temperature may influence oxygenation sensor feedback, in some applications, the system 200 can further include the temperature sensor. More specifically, based on tissue temperature measurements, the processor/controller 206 can calibrate the tissue oxygenation sensor and/or correct raw oxygenation measurement data to compensate for temperature variations. As such, in some configurations, the temperature sensor can be positioned to contact the patient's skin when the tourniquet 10 is deployed. As such, the temperature sensor can be deployed along the bottom surface 262 of the coupling system 204, for example, adjacent the pressure sensor 216. In another example, the temperature sensor can be embedded in one of the (micro) needles of the (micro)needle array. Additionally, while temperature sensing is described in association with tissue oxygenation sensing, temperature sensing may be used in configurations without oxygenation sensing.

The accelerometer can be in communication with the processor/controller 206 and can be configured to measure a level of movement experienced by the limb following tourniquet application. Based on these measurements, the processor/controller 206 can determine tourniquet stability, or additional limb trauma. For example, if there is little to no motion, the accelerometer data would indicate that the subject has not been in motion and that the tourniquet 10 is likely stable. However, sensing of motion can indicate likely greater trauma to the limb (through movement). Accordingly, accelerometer data can be incorporated into either manual or automatic decision-making on when to remove the tourniquet 10. For example, based on the accelerometer data, the processor/controller 206 can adjust the countdown timer or provide an alert or other instructions to the user.

Accordingly, the system 200 of some configurations can include any combination of the above-described sensors and/or additional sensors. For example while pressure and tissue oxygenation measurements can complement each other during and after tourniquet application for monitoring the occlusive effects to ensure proper tourniquet use and improve limb health, some configurations may include only pressure sensing, only oxygen sensing, or a combination of pressure, oxygen, temperature, and/or other sensors incorporated on or in the housing 202. Furthermore, in some configurations, the processor/controller 206 can communicate with remote sensors (not shown), for example, via the transmitter/receiver 212. In one non-limiting example, remote tissue oxygenation sensors can be used to measure tissue oxygenation at other locations along the limb or on the body. In another non-limiting example, blood pressure measurements, via an external sensor, can be communicated to the processor/controller 206. In yet another non-limiting example, the system can include a sensor configured to provide measurements indicative of a circumference of the limb (e.g., based on the overall circumference of the tightened tourniquet). For one configuration of this example, the sensor could be configured with a strip placed around the tourniquet circumference, such that a measurement indicative of circumference could be detected electrically or optically by the sensor.

While the above alerts and warnings are associated with set thresholds or countdown timers related to the sensors, it should be noted that such thresholds or countdown times may be adjusted based on feedback about the patient, either prior to or during application for present use, or after application for future use (e.g., as data learning from outcomes after tourniquet use). In one non-limiting example, the thresholds and countdown times may be personalized to the patient based on information provided to the processor/controller 206 via the user communication module 208, a remote device 214, and/or a remote sensor. Such information can include, but is not limited to, patient limb size (e.g., circumference), blood pressure, optimal occlusion pressure and optimal countdown time, "basic" patient size (e.g., small, medium, large), "specific" patient size (e.g., body mass index, BMI), patient sex, limb type (e.g., arm or leg), limb position, environmental temperature, etc.

Finally, the system 200 can be powered by the power source 224, which may be a battery housed within the housing 202. More specifically, the processor/controller 206 and/or one or more of the user communication module 208, the local storage, the transmitter/receiver 212, the pressure sensor 216, the temperature sensor, and the tissue oxygenation sensor can be connected to the power source 224 in order to power the system 200. In some applications, the battery may be rechargeable, for example, via the USB port 242. For example, in one non-limiting example, the battery may be a rechargeable lithium ion, or lithium ion polymer (LiPo) battery. In other applications, the battery may be rechargeable via self-charging methods, such as the thermoelectric Peltier effect or motion. In yet other applications, the battery may be replaceable. For example, the housing 202, or a portion thereof, can be configured to provide access to the battery for replacement. Such battery can be, for example, a non-rechargeable, long shelf-life alkaline battery, or another suitable rechargeable or single-use battery.

FIGS. 8-11 illustrate another non-limiting example of a system 300 coupled to a tourniquet 10 for use around a limb of a patient. For example, as shown in FIGS. 8-11, the system 300 includes a housing 302, a coupling system 304, a processor/controller 306, a user communication module 308, local storage 310, a transmitter/receiver 312, a pressure sensor 316, a tissue oxygenation sensor (not shown), a tissue oxygenation sensor deployment system (not shown), a temperature sensor (not shown), and a power source 324. Notably, the system 300 may include similar components as the systems 100 200, as described above and illustrated in FIGS. 3-7D, and, thus, such like components will not be further described in detail. In one non-limiting example, the system 304 illustrated in FIGS. 8-11 can measure about 48×48×32 mm³, enabling the system 304 to fit in the palm of a hand, and can weigh about 30 grams.

Generally, the system 300 may differ from the system 200 illustrated in FIGS. 4-6 with respect to the housing 302 and the coupling system 304. For example, the housing 302 can be substantially waterproof and can include a top enclosure 380, a bottom plate 382, and an o-ring 384. The top enclosure 380 can be coupled to the bottom plate 382 via fasteners 386 and threaded inserts 388. The o-ring 284 (such as a water- and steam-resistant o-ring) can be positioned between the top enclosure 380 and the bottom plate 382 in order to substantially seal inside the housing 302 from water, blood, dirt, or other contaminants.

Figure 11:
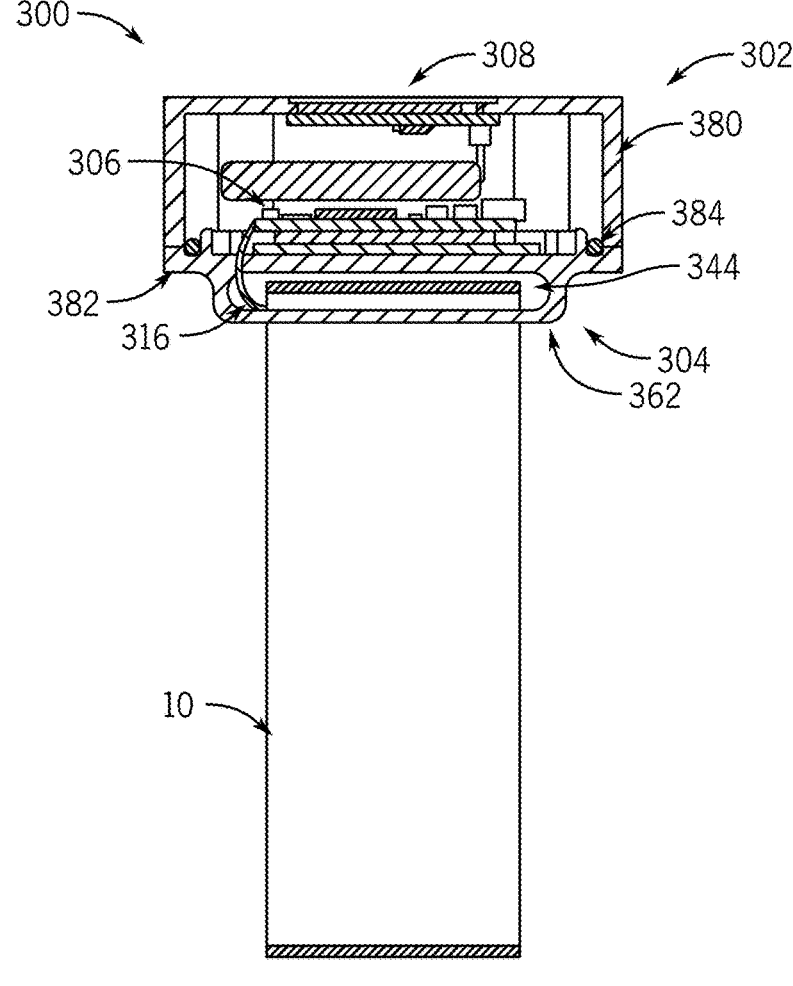
FIG. 11 is a cross-sectional view of the system of FIG. 8, taken along line A-A of FIG. 10.

Furthermore, while the system 200 includes the pressure sensor 216 and/or other sensors positioned along the bottom surface 262 of the coupling system 204, the coupling system 304 of FIGS. 8-11 can internally incorporate such sensors to protect the sensors from water, blood, dirt, or other contaminants. For example, as shown in FIG. 11, the pressure sensor 316 can extend from the housing 302, where it is connected to the circuit board 352, across the mounting passage 344, and into the coupling system 304. Though not specifically shown, the coupling system 304 can further incorporate the tissue oxygenation sensor, the temperature sensor, and/or other sensors, In this manner, the coupling system 304, or at least a bottom portion 390 thereof, may comprise material configured to permit pressure sensing through the material, and/or configured to permit needle arrays to extend through for tissue oxygenation and/or temperature sensing. In some configurations, the bottom portion 390 may comprise substantially flexible material to facilitate better contact with the patient. However, in other configurations, the bottom portion 390 may comprise substantially rigid material. Furthermore, in some configurations, the tissue oxygenation sensor deployment systems described above may instead be coupled to the bottom surface 362 of the coupling system 304.

In light of the above, systems 100, 200, 300 of the present invention can be used in the field when applying an emergency tourniquet 10. Such systems 100, 200, 300 can be retrofitted to existing emergency tourniquets or manufactured with a new tourniquet as a complete smart tourniquet system. The systems 100, 200, 300 can be substantially small and lightweight, permitting individuals to carry the system 100, 200, 300 in their rucksack or pre-attach the system 100, 200, 300 to their standard-issue emergency tourniquet prior to operations. Furthermore, the system 100, 200, 300 can be used for learning or training on proper bleeding control protocols, for example with a mannequin.

Figure 12:
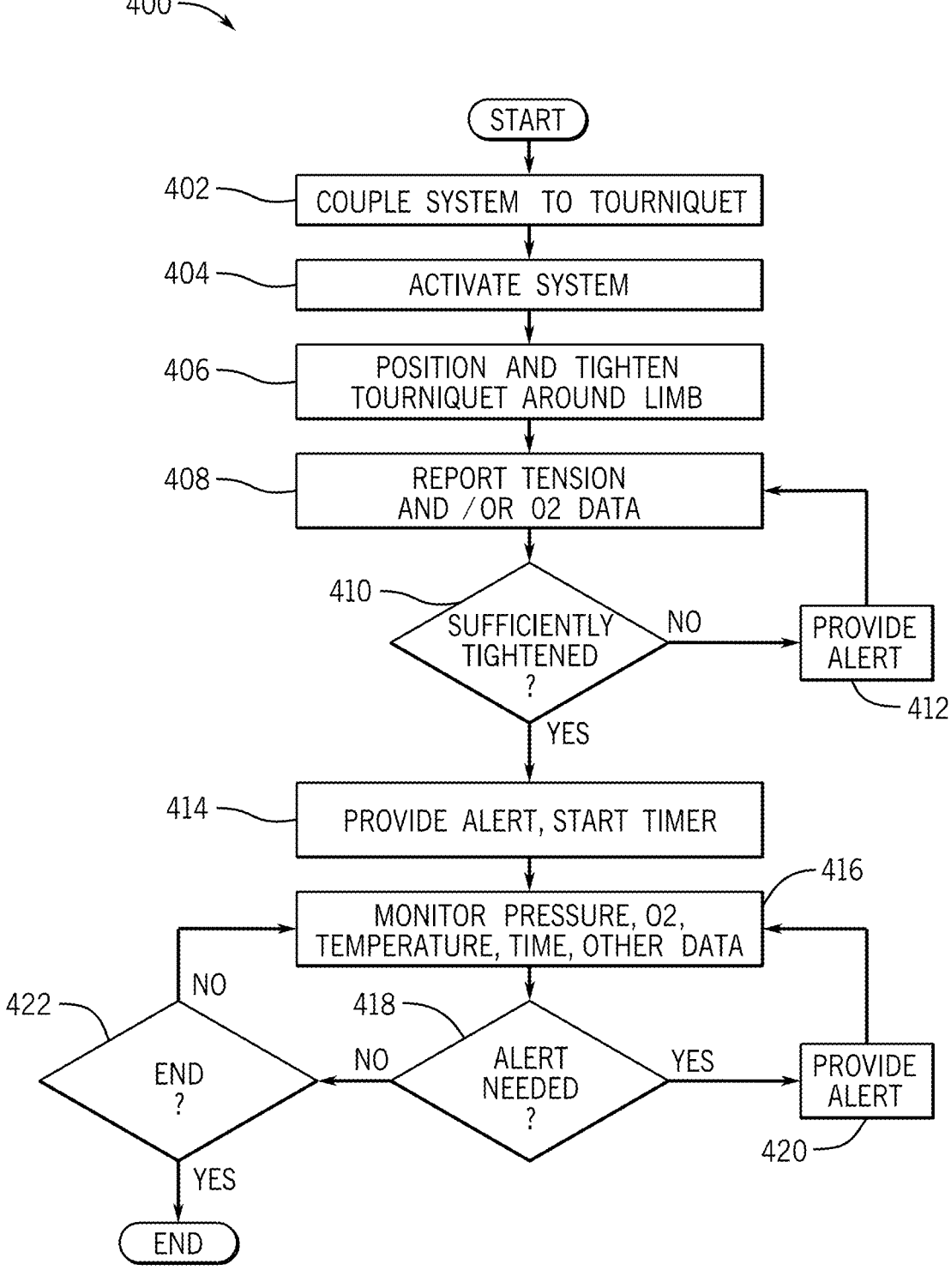
FIG. 12 is a method for tourniquet operation and control using any of the systems of FIGS. 3-11.

According to some applications, the system 100, 200, 300 can be used according to the following method 400, as illustrated in FIG. 12. First, at step 402, the system 100, 200, 300 can be coupled to an emergency tourniquet (e.g., by sliding or clipping the system onto the tourniquet strap). At step 404, the sensors can be activated, for example, by an on/off switch being depressed on the housing 102, 202, 302. In another non-limiting example, sensor activation can be accomplished through a pullout tab. In still another non-limiting example, a switch based on physical tactile touch of the housing 102, 202, 302 could activate the sensors. At step 406, the tourniquet is positioned on the intended body part and tightened. This arrangement causes the pressure sensor, tissue oxygenation sensor, and/or other sensors to be interposed between the tourniquet and the body part. At step 408, real-time tourniquet tension data is reported on the display as the tourniquet is tightened. The system 100, 200, 300 continuously monitors the real-time data to determine when the tourniquet is sufficiently tightened, at step 410. Optionally, if not sufficiently tightened yet, an insufficient tightening alert may be presented at step 412. When sufficient tightening is achieved, an alert is provided to the user via the display and the timer will be activated at step 414. At step 416, pressure (tension), oxygenation, temperature, and/or other data is continuously monitored and logged as well as elapsed time. If an alert or warning is necessary, as determined at step 418, such information is communicated to the user via the display at step 420. Such monitoring will continue until the tourniquet is removed and/or a reset button is depressed on the housing 102, 202, 302, indicating the session has ended (step 422). At any time during the method 400, data or information may be communicated to the user communication module and/or a remote device passively (e.g., real-time data and/or alerts viewable on the visual communication module of the system 100, 200, 300, or communicated to a central hub, such as a user's mobile phone or tablet) or actively (e.g., a user plugging their removable device into the system 100, 200, 300 and requesting to retrieve the data). While the method 400 above is shown and described in a series of steps, it should be noted that, in some configurations, the steps may be executed in a different order shown. For example, step 414 may be executed before step 412 in some applications.

In light of the above, the present invention provides an all-in-one clip-on or slide-on miniature device that can be attached to pre-existing emergency tourniquets for the purpose of monitoring and reporting tissue oxygenation, the amount of force being applied by the tourniquet, and/or other information to a user regardless of the state of the patient.

The present invention has been described in terms of one or more preferred embodiments, and it should be appreciated that many equivalents, alternatives, variations, and modifications, aside from those expressly stated, are possible and within the scope of the invention. Furthermore, the term "about" as used herein means a range of plus or minus 20% with respect to the specified value, more preferably plus or minus 10%, even more preferably plus or minus 5%, most preferably plus or minus 2%. In the alternative, as known in the art, the term "about" indicates a deviation, from the specified value, that is equal to half of a minimum increment of a measure available during the process of measurement of such value with a given measurement tool.

The invention claimed is:

1. A tourniquet monitoring system comprising:
a pressure sensor, wherein the pressure sensor includes a capacitive pressure sensor;
a housing configured to removably engage a tourniquet to position the pressure sensor on a limb of a patient to monitor at least one of deployment or operation of the tourniquet, wherein the pressure sensor is supported by the housing and is configured to contact the limb;
a processor configured to receive feedback from the pressure sensor, compare the feedback to at least one of deployment or operation parameters for the tourniquet, determine a first threshold pressure corresponding to a pressure value necessary for occlusion to sufficiently stop or hinder bleeding, determine a second threshold pressure corresponding to a pressure value for complete occlusion of blood flow through the limb, monitor an elapsed time from when the tourniquet reaches a pressure between the first threshold pressure and the second threshold pressure, and generate a user report; and
a user communication module configured to communicate the user report.

2. The system of claim 1, wherein the capacitive pressure sensor is configured to be arranged between the tourniquet and a patient wearing the tourniquet when the housing is engaged with the tourniquet.

3. The system of claim 2, wherein the capacitive pressure sensor is configured to be compressed as the tourniquet is tightened against the patient.

4. The system of claim 2, wherein the housing includes a mounting passage configured to receive the tourniquet to secure the housing to the tourniquet and arrange the capacitive pressure sensor between the tourniquet and the patient.

5. The system of claim 2, wherein the processor is configured to monitor a pressure applied by the tourniquet on the patient based on the feedback from the capacitive pressure sensor.

6. The system of claim 5, wherein the user report includes real-time pressure reports indicating the pressure applied by the tourniquet on the patient.

7. The system of claim 5, wherein the user report includes a pressure alert when the pressure applied by the tourniquet on the limb is below the first threshold pressure or above the second threshold pressure.

8. The system of claim 5, wherein the user report includes one of a visual, graphic, audible, or tactile indication communicating when the pressure applied by the tourniquet on the limb is (i) below the first threshold pressure or above the second threshold pressure or (ii) between the first threshold pressure and the second threshold pressure.

9. The system of claim 1, further comprising an oxygenation sensor configured to monitor oxygenation of the tissue proximate to the tourniquet when the tourniquet is engaged with the limb.

10. The system of claim 9, wherein the processor is configured to analyze the feedback from the oxygenation sensor to determine the oxygenation of the tissue proximate to the tourniquet and generate an oxygenation alert communicated to a user via the user communication module if the oxygenation of the tissue proximate to the tourniquet is outside a desired range.

11. The system of claim 9, wherein the oxygenation sensor includes at least one of a spectroscopic sensor or a lifetime sensor configured to monitor tissue proximate to the tourniquet when the tourniquet is engaged with a patient.

12. The system of claim 11, wherein the oxygenation sensor includes a needle configured to extend the at least one of the spectroscopic sensor or the lifetime sensor into the tissue when the tourniquet is deployed on the patient.

13. The system of claim 12, wherein the at least one of the spectroscopic sensor or the lifetime sensor includes at least one of a plurality of spectroscopic sensors or a plurality of lifetime sensors, and further comprising a plurality of needles configured to extend the plurality of spectroscopic sensors or the plurality of lifetime sensors into the tissue when the tourniquet is deployed on the patient.

14. The system of claim 13, wherein each of the plurality of needles is a microneedle and the plurality of needles forms an array of microneedles.

15. The system of claim 13, wherein the plurality of needles is arranged within a needle housing and extends into the tissue of the patient as the tourniquet is tightened about the patient.

16. The system of claim 15, wherein the needle housing is formed of a foam configured to compress as the tourniquet is tightened about the patient.

17. The system of claim 1, further comprising a temperature sensor configured to monitor a temperature of tissue proximate to the tourniquet when a patient is wearing the tourniquet.

18. The system of claim 1, wherein the user communication module includes at least one of a display, a speaker, and a tactile module.

19. The system of claim 1, further comprising at least one of a communications port or a wireless communications system configured to communicate to a remote device.

20. The system of claim 1, wherein the processor is configured to analyze the feedback from the pressure sensor to determine a change in a rate of change in the feedback from the pressure sensor.

21. The system of claim 1, wherein the housing includes a coupling system configured to one of clip on or slide onto a sleeve of the tourniquet.

22. The system of claim 21, wherein the coupling system is a u-shaped structure defining a mounting passage through which the sleeve of the tourniquet is fed to removably engage the tourniquet with the housing.

23. The system of claim 1, wherein the pressure sensor includes an accelerometer configured to monitor movement of the tourniquet when a patient is wearing the tourniquet.

24. The tourniquet of claim 1, wherein monitoring the elapsed time includes a countdown from one or more threshold numbers.

25. The tourniquet of claim 24, wherein the one or more threshold numbers includes a maximum tourniquet time or an extended tourniquet time corresponding to the time the tourniquet is positioned on the limb.

26. The tourniquet of claim 25, wherein the processor is further configured to provide one or more time alerts corresponding to the countdown reaching the one or more threshold numbers.

27. A method for monitoring an occlusive effect of a tourniquet on a human limb, the method comprising:

providing a tourniquet;

retrofitting a system onto the tourniquet by removably attaching a housing of the system to the tourniquet, the system including:

the housing, a capacitive pressure sensor supported by the housing, a processor, and a user communication module;

tightening the tourniquet around the human limb so that the capacitive pressure sensor contacts the human limb and is interposed between the tourniquet and the human limb;

sensing a compressive force between the tourniquet and the human limb via the capacitive pressure sensor;

determining a first threshold pressure of the tourniquet corresponding to a pressure value necessary for occlusion to sufficiently stop or hinder bleeding, determining a second threshold pressure of the tourniquet corresponding to a pressure value for complete occlusion of blood flow through the human limb;

monitoring an elapsed time from when the tourniquet reaches a pressure between the first threshold pressure and the second threshold pressure; and communicating a user report via the user communication module, the user report including at least one of the compressive force and the elapsed time.

28. The method of claim 27, wherein the system includes an oxygenation sensor; and further comprising tightening the tourniquet around the human limb so that the oxygenation sensor contacts tissue of the human limb; and sensing an oxygenation level of the tissue, wherein the user report further includes the oxygenation level.

29. The method of claim 27, further comprising analyzing the compressive force to determine when the tourniquet is sufficiently tightened, wherein the user report includes a pressure alert that the tourniquet is below the first threshold pressure or above the second threshold pressure.

30. The method of claim 27, wherein communicating the user report includes at least one of displaying one of text or graphics on a screen, illuminating one or more LEDs, providing an audible indication, and providing a tactile response.

31. The method of claim 27, further comprising transmitting the user report to a remote device, remote from the system.

32. A tourniquet system for use on a human limb, comprising:

a field tourniquet;

a housing configured to removably engage the tourniquet;

a capacitive pressure sensor positioned relative to the housing and the tourniquet so the pressure sensor is configured to contact the human limb and is interposed between the tourniquet and the human limb for sensing compressive force therebetween when the housing is engaged with the tourniquet;

an oxygenation sensor positioned relative to the housing and the tourniquet so the oxygenation sensor is interposed between the tourniquet and the human limb for sensing oxygen levels of the human limb when housing is engaged with the tourniquet;

a processor configured to receive feedback from the capacitive pressure sensor and the oxygenation sensor, compare the feedback to at least one of deployment or operation parameters for the tourniquet, determine a first threshold of the tourniquet corresponding to a pressure value necessary for occlusion to sufficiently stop or hinder bleeding, determine a second threshold pressure of the tourniquet corresponding to a pressure value for complete occlusion of blood flow through the human limb, monitor an elapsed time from when the tourniquet reaches a pressure between the first threshold pressure and the second threshold pressure, and generate a user report; and a user communication module configured to communicate the user report.

\* \* \* \* \*